(12) United States Patent
Abbate

(10) Patent No.: US 10,406,332 B2
(45) Date of Patent: Sep. 10, 2019

(54) SYSTEMS, DEVICES, AND METHOD FOR TREATING A SINUS CONDITION

(71) Applicant: Intersect ENT, Inc., Menlo Park, CA (US)

(72) Inventor: Anthony J. Abbate, Santa Clara, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 0 days.

(21) Appl. No.: 14/210,078

(22) Filed: Mar. 13, 2014

(65) Prior Publication Data

US 2014/0276408 A1 Sep. 18, 2014

Related U.S. Application Data

(60) Provisional application No. 61/785,939, filed on Mar. 14, 2013.

(51) Int. Cl.
*A61M 29/00* (2006.01)
*A61F 2/18* (2006.01)
*A61F 2/82* (2013.01)
*A61M 31/00* (2006.01)
(Continued)

(52) U.S. Cl.
CPC ............. *A61M 29/00* (2013.01); *A61F 2/186* (2013.01); *A61F 2/82* (2013.01); *A61M 31/002* (2013.01); *A61F 5/08* (2013.01); *A61F 2002/9522* (2013.01); *A61F 2210/0004* (2013.01);
(Continued)

(58) Field of Classification Search
CPC .... A61F 2/04; A61F 2/186; A61F 2002/9522; A61F 2210/0004; A61F 2230/0067; A61F 2250/0067; A61F 2/82; A61F 5/08; A61M 2205/04; A61M 29/00; A61M 31/002
See application file for complete search history.

(56) References Cited

U.S. PATENT DOCUMENTS

| 374,026 | A | 11/1887 | Williams |
| 2,009,393 | A | 7/1935 | Failla |
| 2,096,162 | A | 10/1937 | Daley |

(Continued)

FOREIGN PATENT DOCUMENTS

| AU | 2008/201495 A1 | 10/2008 |
| CN | 101189016 A | 5/2008 |

(Continued)

OTHER PUBLICATIONS

Becker, D.G. (2003). "The Minimally Invasive, Endoscopic Approach to Sinus Surgery," *Journal of Long-Term Effects of Medical Implants* 13(3):207-221.

(Continued)

*Primary Examiner* — Imani N Hayman
(74) *Attorney, Agent, or Firm* — Cooley LLP

(57) ABSTRACT

Systems, devices, and methods may be used for delivery of an implant to a bodily cavity. The implant may include a hub and a plurality of legs, and may be moveable between a low-profile and expanded configuration. The systems may include a crimping device having a crimping member with a plurality of arms. The plurality of arms may engage the plurality of legs of the implant, and may move the legs to move the implant to the low-profile configuration. In some instances a delivery device may aid in crimping and/or delivery of the implant.

13 Claims, 15 Drawing Sheets

(51) Int. Cl.
    *A61F 2/95*          (2013.01)
    *A61F 5/08*          (2006.01)
(52) U.S. Cl.
    CPC ............ *A61F 2230/0067* (2013.01); *A61F 2250/0067* (2013.01); *A61M 2205/04* (2013.01)

(56) References Cited

U.S. PATENT DOCUMENTS

| | | |
|---|---|---|
| 2,691,985 A | 10/1954 | Newsom |
| 3,049,125 A | 8/1962 | Kriwkowitsch |
| 3,473,165 A | 10/1969 | Gran et al. |
| 3,502,078 A | 3/1970 | Hill et al. |
| 3,517,128 A | 3/1970 | Hines |
| 3,570,494 A | 3/1971 | Gottschalk |
| 3,583,391 A | 6/1971 | Cox et al. |
| 3,766,924 A | 10/1973 | Pidgeon |
| 3,800,788 A | 4/1974 | White |
| 3,828,577 A | 8/1974 | Haynes |
| 3,894,539 A | 7/1975 | Tallent |
| 3,903,893 A | 9/1975 | Scheer |
| 3,913,584 A | 10/1975 | Walchle et al. |
| 4,094,303 A | 6/1978 | Johnston |
| 4,245,652 A | 1/1981 | Kelly et al. |
| 4,389,208 A | 6/1983 | LeVeen et al. |
| 4,419,095 A | 12/1983 | Nebergall et al. |
| D276,937 S | 12/1984 | Griggs |
| 4,534,761 A | 8/1985 | Raible |
| 4,580,568 A | 4/1986 | Gianturco |
| 4,604,920 A | 8/1986 | Dupke |
| 4,627,971 A | 12/1986 | Ayer |
| 4,650,488 A | 3/1987 | Bays et al. |
| 4,655,771 A | 4/1987 | Wallsten |
| 4,704,126 A | 11/1987 | Baswell et al. |
| 4,737,141 A | 4/1988 | Spits |
| 4,744,792 A | 5/1988 | Sander et al. |
| 4,753,636 A | 6/1988 | Free |
| 4,886,493 A | 12/1989 | Yee |
| 4,941,881 A | 7/1990 | Masters et al. |
| 4,964,850 A | 10/1990 | Bouton et al. |
| 5,000,957 A | 3/1991 | Eckenhoff et al. |
| 5,011,474 A | 4/1991 | Brennan |
| 5,035,706 A | 7/1991 | Giantureo et al. |
| 5,062,829 A | 11/1991 | Pryor et al. |
| 5,108,418 A | 4/1992 | Lefebvre |
| 5,116,311 A | 5/1992 | Löfstedt |
| 5,139,502 A | 8/1992 | Berg et al. |
| 5,139,510 A | 8/1992 | Goldsmith, III et al. |
| 5,139,832 A | 8/1992 | Hayashi et al. |
| 5,167,614 A | 12/1992 | Tessmann et al. |
| 5,189,110 A | 2/1993 | Ikematu et al. |
| 5,217,484 A | 6/1993 | Marks |
| 5,246,455 A | 9/1993 | Shikani |
| 5,256,146 A | 10/1993 | Ensminger et al. |
| 5,300,119 A | 4/1994 | Blom |
| 5,312,813 A | 5/1994 | Costerton et al. |
| 5,324,304 A | 6/1994 | Rasmussen |
| 5,336,163 A | 8/1994 | DeMane et al. |
| 5,342,296 A | 8/1994 | Persson et al. |
| 5,344,427 A | 9/1994 | Cottenceau et al. |
| 5,348,553 A | 9/1994 | Whitney |
| 5,350,580 A | 9/1994 | Muchow et al. |
| 5,391,179 A | 2/1995 | Mezzoli |
| 5,443,498 A | 8/1995 | Fontaine |
| 5,501,700 A | 3/1996 | Hirata |
| 5,507,210 A | 4/1996 | Paramest |
| 5,507,807 A | 4/1996 | Shippert |
| 5,512,055 A | 4/1996 | Domb et al. |
| 5,538,738 A | 7/1996 | Ritter et al. |
| 5,540,712 A | 7/1996 | Kleshinski et al. |
| 5,556,413 A | 9/1996 | Lam |
| 5,632,762 A | 5/1997 | Myler |
| 5,634,942 A | 6/1997 | Chevillon et al. |
| 5,645,584 A | 7/1997 | Suyama |
| 5,664,567 A | 9/1997 | Linder |
| 5,669,933 A | 9/1997 | Simon et al. |
| 5,672,179 A | 9/1997 | Garth et al. |
| 5,693,065 A | 12/1997 | Rains, III |
| 5,713,855 A | 2/1998 | Shippert |
| 5,725,525 A * | 3/1998 | Kordis ............... A61B 5/0422 600/372 |
| 5,746,224 A | 5/1998 | Edwards |
| 5,749,921 A | 5/1998 | Lenker et al. |
| 5,792,100 A | 8/1998 | Shantha |
| 5,800,379 A | 9/1998 | Edwards |
| 5,800,429 A | 9/1998 | Edwards |
| 5,827,224 A | 10/1998 | Shippert |
| 5,895,408 A | 4/1999 | Pagan |
| 5,899,878 A | 5/1999 | Glassman |
| 5,928,190 A | 7/1999 | Davis |
| 5,931,852 A | 8/1999 | Brennan |
| 5,968,071 A | 10/1999 | Chevillon et al. |
| 5,992,000 A | 11/1999 | Humphrey et al. |
| 6,033,436 A | 3/2000 | Steinke et al. |
| 6,054,122 A | 4/2000 | MacPhee et al. |
| 6,063,102 A | 5/2000 | Morales |
| 6,074,381 A | 6/2000 | Dinh et al. |
| 6,082,990 A | 7/2000 | Jackson et al. |
| 6,092,273 A | 7/2000 | Villareal |
| 6,092,528 A | 7/2000 | Edwards |
| 6,108,886 A | 8/2000 | Kimes et al. |
| 6,113,641 A | 9/2000 | Leroy et al. |
| 6,123,697 A | 9/2000 | Shippert |
| 6,149,681 A | 11/2000 | Houser et al. |
| 6,149,944 A | 11/2000 | Jeong et al. |
| 6,152,946 A | 11/2000 | Broome et al. |
| 6,180,848 B1 | 1/2001 | Flament et al. |
| 6,190,353 B1 | 2/2001 | Makower et al. |
| 6,195,225 B1 | 2/2001 | Komatsu et al. |
| 6,200,335 B1 | 3/2001 | Igaki |
| 6,217,600 B1 | 4/2001 | DiMatteo |
| 6,224,626 B1 | 5/2001 | Steinke |
| 6,228,111 B1 | 5/2001 | Törmälä et al. |
| 6,280,413 B1 | 8/2001 | Clark et al. |
| 6,290,728 B1 | 9/2001 | Phelps et al. |
| 6,297,227 B1 | 10/2001 | Johnson |
| 6,302,875 B1 | 10/2001 | Makower et al. |
| 6,306,084 B1 | 10/2001 | Pinczower |
| 6,329,386 B1 | 12/2001 | Mollison |
| 6,342,068 B1 | 1/2002 | Thompson |
| 6,347,241 B2 | 2/2002 | Burbank et al. |
| 6,350,465 B1 | 2/2002 | Jonnalagadda et al. |
| 6,352,547 B1 | 3/2002 | Brown et al. |
| 6,355,032 B1 | 3/2002 | Hovda et al. |
| 6,375,615 B1 | 4/2002 | Flaherty et al. |
| 6,386,197 B1 | 5/2002 | Miller |
| 6,398,758 B1 | 6/2002 | Jacobsen et al. |
| 6,447,530 B1 | 9/2002 | Ostrovsky et al. |
| 6,447,539 B1 | 9/2002 | Nelson et al. |
| 6,468,290 B1 | 10/2002 | Weldon et al. |
| 6,491,940 B1 | 12/2002 | Levin |
| 6,524,608 B2 | 2/2003 | Ottoboni et al. |
| 6,537,294 B1 | 3/2003 | Boyle et al. |
| 6,543,452 B1 | 4/2003 | Lavigne |
| 6,544,230 B1 | 4/2003 | Flaherty et al. |
| 6,555,566 B2 | 4/2003 | Ponikau |
| 6,562,058 B2 | 5/2003 | Seguin et al. |
| 6,565,597 B1 | 5/2003 | Fearnot et al. |
| 6,589,286 B1 | 7/2003 | Litner |
| 6,605,294 B2 | 8/2003 | Sawhney |
| 6,606,995 B1 | 8/2003 | Sadek et al. |
| 6,618,921 B1 | 9/2003 | Thornton |
| 6,685,648 B2 | 2/2004 | Flaherty et al. |
| 6,692,455 B2 | 2/2004 | Goode et al. |
| 6,695,856 B2 | 2/2004 | Kieturakis et al. |
| 6,709,465 B2 | 3/2004 | Mitchell et al. |
| 6,712,859 B2 | 3/2004 | Rousseau et al. |
| 6,715,485 B1 | 4/2004 | Djupesland |
| 6,719,934 B2 | 4/2004 | Stinson |
| 6,746,426 B1 | 6/2004 | Flaherty et al. |
| 6,749,617 B1 | 6/2004 | Palasis et al. |
| 6,884,260 B2 | 4/2005 | Kugler et al. |
| 6,942,690 B1 | 9/2005 | Pollock et al. |
| 6,945,992 B2 | 9/2005 | Goodson, IV et al. |

(56) References Cited

U.S. PATENT DOCUMENTS

| | | |
|---|---|---|
| 6,951,053 B2 | 10/2005 | Padilla et al. |
| 6,966,923 B2 | 11/2005 | Gittings |
| 7,018,401 B1 | 3/2006 | Hyodoh et al. |
| 7,072,720 B2 | 7/2006 | Puskas |
| 7,074,426 B2 | 7/2006 | Kochinke |
| 7,108,706 B2 | 9/2006 | Hogle |
| RE39,321 E | 10/2006 | MacPhee et al. |
| 7,179,275 B2 | 2/2007 | McGuckin, Jr. et al. |
| 7,195,016 B2 | 3/2007 | Loyd et al. |
| 7,225,518 B2 | 6/2007 | Eidenschink et al. |
| 7,235,099 B1 | 6/2007 | Duncavage et al. |
| 7,249,390 B2 | 7/2007 | Yale et al. |
| RE39,923 E | 11/2007 | Blom |
| 7,314,484 B2 | 1/2008 | Deem et al. |
| 7,316,147 B2 | 1/2008 | Perreault et al. |
| 7,361,168 B2 | 4/2008 | Makower et al. |
| 7,410,480 B2 | 8/2008 | Muni et al. |
| 7,419,497 B2 | 9/2008 | Muni et al. |
| 7,451,765 B2 | 11/2008 | Adler |
| 7,462,175 B2 | 12/2008 | Chang et al. |
| 7,476,648 B1 | 1/2009 | Tabata et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,559,925 B2 | 7/2009 | Goldfarb et al. |
| 7,641,644 B2 | 1/2010 | Chang et al. |
| 7,641,688 B2 | 1/2010 | Lesh |
| 7,645,272 B2 | 1/2010 | Chang et al. |
| 7,651,696 B2 | 1/2010 | Bates |
| 7,654,997 B2 | 2/2010 | Makower et al. |
| 7,658,758 B2 | 2/2010 | Diaz et al. |
| 7,658,764 B2 | 2/2010 | Reitan et al. |
| 7,662,141 B2 | 2/2010 | Eaton et al. |
| 7,662,142 B2 | 2/2010 | Eaton et al. |
| 7,686,798 B2 | 3/2010 | Eaton et al. |
| 7,691,094 B2 | 4/2010 | Eaton et al. |
| 7,713,255 B2 | 5/2010 | Eaton et al. |
| 7,717,933 B2 | 5/2010 | Becker |
| 7,740,642 B2 | 6/2010 | Becker |
| 7,753,929 B2 | 7/2010 | Becker |
| 7,771,482 B1 | 8/2010 | Karmon |
| 7,951,130 B2 | 5/2011 | Eaton et al. |
| 7,951,131 B2 | 5/2011 | Eaton et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,007,470 B2 | 8/2011 | Shirley et al. |
| 8,025,635 B2 | 9/2011 | Eaton et al. |
| 8,088,120 B2 | 1/2012 | Worsoff |
| 8,109,918 B2 | 2/2012 | Eaton et al. |
| 8,192,450 B2 | 6/2012 | Gonzales et al. |
| 8,197,433 B2 | 6/2012 | Cohen |
| 8,303,640 B2 | 11/2012 | Hepworth et al. |
| 8,337,454 B2 | 12/2012 | Eaton et al. |
| 8,500,776 B2 | 8/2013 | Ebner |
| 8,535,707 B2 | 9/2013 | Arensdorf et al. |
| 8,585,730 B2 | 11/2013 | Eaton et al. |
| 8,585,731 B2 | 11/2013 | Abbate et al. |
| 8,585,753 B2 | 11/2013 | Scanlon et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,763,222 B2 | 7/2014 | Abbate et al. |
| 8,802,131 B2 | 8/2014 | Arensdorf et al. |
| 8,858,974 B2 | 10/2014 | Eaton et al. |
| 8,986,341 B2 | 3/2015 | Abbate et al. |
| 9,585,681 B2 | 3/2017 | Eaton et al. |
| 10,232,152 B2 | 3/2019 | Abbate |
| 2001/0021871 A1 | 9/2001 | Stinson |
| 2002/0022048 A1 | 2/2002 | Bromberg |
| 2002/0051793 A1 | 5/2002 | Drabick |
| 2002/0051845 A1 | 5/2002 | Mehta et al. |
| 2002/0077693 A1 | 6/2002 | Barclay et al. |
| 2002/0111603 A1 | 8/2002 | Cheikh |
| 2002/0143387 A1 | 10/2002 | Soetikno et al. |
| 2002/0188344 A1 | 12/2002 | Bolea et al. |
| 2002/0198586 A1 | 12/2002 | Inoue |
| 2003/0040772 A1 | 2/2003 | Hyodoh et al. |
| 2003/0055488 A1 | 3/2003 | Igaki |
| 2003/0065346 A1 | 4/2003 | Evens et al. |
| 2003/0070682 A1 | 4/2003 | Wilson et al. |
| 2003/0105469 A1 | 6/2003 | Karmon |
| 2003/0133877 A1 | 7/2003 | Levin |
| 2003/0135266 A1 | 7/2003 | Chew et al. |
| 2003/0135268 A1 | 7/2003 | Desai |
| 2003/0135970 A1 | 7/2003 | Thornton |
| 2003/0147954 A1 | 8/2003 | Yang et al. |
| 2003/0158598 A1 | 8/2003 | Ashton |
| 2003/0195459 A1 | 10/2003 | Shippert |
| 2003/0203030 A1 | 10/2003 | Ashton et al. |
| 2003/0209835 A1 | 11/2003 | Chun et al. |
| 2003/0236570 A1 | 12/2003 | Cook et al. |
| 2004/0043052 A1 | 3/2004 | Hunter et al. |
| 2004/0064083 A1 | 4/2004 | Becker |
| 2004/0064150 A1 | 4/2004 | Becker |
| 2004/0093062 A1 | 5/2004 | Glastra |
| 2004/0116958 A1 | 6/2004 | Gopferich et al. |
| 2004/0117004 A1 | 6/2004 | Osborne et al. |
| 2004/0133270 A1 | 7/2004 | Grandt |
| 2004/0176827 A1 | 9/2004 | Jacobson et al. |
| 2004/0236415 A1 | 11/2004 | Thomas |
| 2005/0038497 A1 | 2/2005 | Neuendorf et al. |
| 2005/0043706 A1 | 2/2005 | Eaton et al. |
| 2005/0043783 A1 | 2/2005 | Amis et al. |
| 2005/0055045 A1 | 3/2005 | DeVries et al. |
| 2005/0119725 A1 | 6/2005 | Wang et al. |
| 2005/0124560 A1 | 6/2005 | Sung et al. |
| 2005/0131460 A1 | 6/2005 | Gilford |
| 2005/0131514 A1 | 6/2005 | Hijlkema et al. |
| 2005/0131524 A1 | 6/2005 | Majercak et al. |
| 2005/0131525 A1 | 6/2005 | Hartley |
| 2005/0143817 A1 | 6/2005 | Hunter et al. |
| 2005/0163821 A1 | 7/2005 | Sung et al. |
| 2005/0165347 A1 | 7/2005 | Bardy |
| 2005/0203605 A1 | 9/2005 | Dolan |
| 2005/0229670 A1 | 10/2005 | Perreault |
| 2005/0234503 A1 | 10/2005 | Ravenscroft et al. |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0106417 A1 | 5/2006 | Tessmer et al. |
| 2006/0135981 A1 | 6/2006 | Lenker et al. |
| 2006/0142736 A1 | 6/2006 | Hissink et al. |
| 2006/0162722 A1 | 7/2006 | Boehm et al. |
| 2006/0167540 A1 | 7/2006 | Masters et al. |
| 2006/0210605 A1 | 9/2006 | Chang et al. |
| 2006/0247499 A1 | 11/2006 | Butler et al. |
| 2006/0265042 A1 | 11/2006 | Catanese, III et al. |
| 2006/0276871 A1 | 12/2006 | Lamson et al. |
| 2007/0005094 A1 | 1/2007 | Eaton et al. |
| 2007/0055348 A1 | 3/2007 | Pryor |
| 2007/0079494 A1 | 4/2007 | Serrano |
| 2007/0100435 A1 | 5/2007 | Case et al. |
| 2007/0106366 A1 | 5/2007 | Delaloye et al. |
| 2007/0112373 A1 | 5/2007 | Carr et al. |
| 2007/0129751 A1 | 6/2007 | Muni et al. |
| 2007/0131525 A1 | 6/2007 | Lu et al. |
| 2007/0135789 A1 | 6/2007 | Chang et al. |
| 2007/0156211 A1 | 7/2007 | Ferren et al. |
| 2007/0162100 A1 | 7/2007 | Gabbay |
| 2007/0167682 A1 | 7/2007 | Goldfarb et al. |
| 2007/0179599 A1 | 8/2007 | Brodbeck et al. |
| 2007/0191922 A1 | 8/2007 | Hartley |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0227544 A1 | 10/2007 | Betsy et al. |
| 2007/0233225 A1 | 10/2007 | Rapacki et al. |
| 2007/0249896 A1 | 10/2007 | Goldfarb et al. |

(56) References Cited

U.S. PATENT DOCUMENTS

| | | |
|---|---|---|
| 2007/0250105 A1 | 10/2007 | Ressemann et al. |
| 2007/0269385 A1 | 11/2007 | Yun et al. |
| 2007/0270941 A1 | 11/2007 | Headley et al. |
| 2007/0282305 A1 | 12/2007 | Goldfarb et al. |
| 2007/0289677 A1 | 12/2007 | Ma et al. |
| 2007/0293726 A1 | 12/2007 | Goldfarb et al. |
| 2007/0293727 A1 | 12/2007 | Goldfarb et al. |
| 2007/0293946 A1 | 12/2007 | Gonzales et al. |
| 2007/0297186 A1 | 12/2007 | Hoover et al. |
| 2007/0299043 A1 | 12/2007 | Hunter et al. |
| 2008/0015540 A1 | 1/2008 | Muni et al. |
| 2008/0027481 A1 | 1/2008 | Gilson et al. |
| 2008/0053458 A1 | 3/2008 | De Silva |
| 2008/0058295 A1 | 3/2008 | Chaudry |
| 2008/0058296 A1 | 3/2008 | Chaudry |
| 2008/0069858 A1 | 3/2008 | Weber |
| 2008/0077226 A1 | 3/2008 | Ouellette et al. |
| 2008/0077230 A1 | 3/2008 | Heaney et al. |
| 2008/0082162 A1 | 4/2008 | Boismier et al. |
| 2008/0085293 A1 | 4/2008 | Yang |
| 2008/0089952 A1 | 4/2008 | Hunter et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0097568 A1 | 4/2008 | Savage et al. |
| 2008/0097575 A1 | 4/2008 | Cottone |
| 2008/0097576 A1 | 4/2008 | Cottone et al. |
| 2008/0097580 A1 | 4/2008 | Dave |
| 2008/0097581 A1 | 4/2008 | Shanley |
| 2008/0097591 A1 | 4/2008 | Savage et al. |
| 2008/0103361 A1 | 5/2008 | Makower et al. |
| 2008/0103521 A1 | 5/2008 | Makower et al. |
| 2008/0103584 A1 | 5/2008 | Su et al. |
| 2008/0113000 A1 | 5/2008 | Hunter et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0145514 A1 | 6/2008 | Hunter et al. |
| 2008/0154237 A1 | 6/2008 | Chang et al. |
| 2008/0154250 A1 | 6/2008 | Makower et al. |
| 2008/0183128 A1 | 7/2008 | Morriss et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0262593 A1 | 10/2008 | Ryan et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306579 A1 | 12/2008 | Dolan et al. |
| 2008/0319424 A1 | 12/2008 | Muni et al. |
| 2009/0004272 A1 | 1/2009 | Gibson et al. |
| 2009/0004273 A1 | 1/2009 | Gibson et al. |
| 2009/0005763 A1 | 1/2009 | Makower et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0035351 A1 | 2/2009 | Berglund et al. |
| 2009/0036968 A1 | 2/2009 | Hepworth et al. |
| 2009/0036974 A1 | 2/2009 | Penn et al. |
| 2009/0041824 A1 | 2/2009 | Zugates et al. |
| 2009/0047326 A1 | 2/2009 | Eaton et al. |
| 2009/0047327 A1 | 2/2009 | Eaton et al. |
| 2009/0050145 A1 | 2/2009 | De Silva et al. |
| 2009/0056709 A1 | 3/2009 | Worsoff |
| 2009/0093823 A1 | 4/2009 | Chang et al. |
| 2009/0156980 A1 | 6/2009 | Eaton et al. |
| 2009/0177272 A1 | 7/2009 | Abbate et al. |
| 2009/0182371 A1 | 7/2009 | Clausen et al. |
| 2009/0187098 A1 | 7/2009 | Makower et al. |
| 2009/0187211 A1 | 7/2009 | Mackiewicz |
| 2009/0192488 A1 | 7/2009 | Eaton et al. |
| 2009/0192489 A1 | 7/2009 | Eaton et al. |
| 2009/0192490 A1 | 7/2009 | Eaton et al. |
| 2009/0192491 A1 | 7/2009 | Eaton et al. |
| 2009/0192492 A1 | 7/2009 | Eaton et al. |
| 2009/0198179 A1 | 8/2009 | Abbate et al. |
| 2009/0198216 A1 | 8/2009 | Muni et al. |
| 2009/0220571 A1 | 9/2009 | Eaton et al. |
| 2009/0227945 A1 | 9/2009 | Eaton et al. |
| 2009/0238859 A1 | 9/2009 | Eaton et al. |
| 2009/0240112 A1 | 9/2009 | Goldfarb et al. |
| 2009/0306624 A1 | 12/2009 | Arensdorf et al. |
| 2009/0312745 A1 | 12/2009 | Goldfarb et al. |
| 2010/0043197 A1 | 2/2010 | Abbate et al. |
| 2011/0004192 A1 | 1/2011 | Eaton et al. |
| 2011/0004193 A1 | 1/2011 | Eaton et al. |
| 2011/0004194 A1 | 1/2011 | Eaton et al. |
| 2011/0004195 A1 | 1/2011 | Eaton et al. |
| 2011/0004196 A1 | 1/2011 | Eaton et al. |
| 2011/0015612 A1 | 1/2011 | Arcand et al. |
| 2011/0021986 A1 | 1/2011 | Zamboni |
| 2011/0066135 A1 | 3/2011 | Eaton et al. |
| 2011/0125091 A1 | 5/2011 | Abbate |
| 2011/0167964 A1 | 7/2011 | Price |
| 2012/0101429 A1 | 4/2012 | Eaton et al. |
| 2013/0041463 A1 | 2/2013 | Ressemann |
| 2013/0066358 A1 | 3/2013 | Nalluri et al. |
| 2013/0231693 A1 | 9/2013 | Edgren et al. |
| 2013/0245608 A1 | 9/2013 | Muni et al. |
| 2013/0253567 A1 | 10/2013 | Edgren et al. |
| 2013/0281982 A1 | 10/2013 | Makower et al. |
| 2013/0304232 A1 | 11/2013 | Gries |
| 2014/0018839 A1 | 1/2014 | Renner et al. |
| 2014/0074065 A1 | 3/2014 | Muni et al. |
| 2014/0074238 A1 | 3/2014 | Abbate et al. |
| 2014/0079755 A1 | 3/2014 | Eaton et al. |
| 2014/0107615 A1 | 4/2014 | Doshi et al. |
| 2014/0276408 A1 | 9/2014 | Abbate |
| 2014/0283349 A1 | 9/2014 | Abbate et al. |
| 2014/0324025 A1 | 10/2014 | Arensdorf et al. |
| 2015/0081017 A1 | 3/2015 | Abbate et al. |
| 2016/0144158 A1 | 5/2016 | Abbate |
| 2016/0287854 A1 | 10/2016 | Eaton et al. |

FOREIGN PATENT DOCUMENTS

| | | |
|---|---|---|
| CN | 102573981 A | 7/2012 |
| DE | 101 05 592 A1 | 8/2002 |
| EP | 0 096 941 B1 | 9/1986 |
| EP | 0 423 916 A1 | 4/1991 |
| EP | 0 761 251 A1 | 3/1997 |
| EP | 0 938 880 A2 | 9/1999 |
| EP | 1 415 671 A1 | 5/2004 |
| EP | 1 870 057 A1 | 12/2007 |
| EP | 2 754 463 | 7/2014 |
| FR | 2 916 135 A1 | 11/2008 |
| GB | 165 537 A | 6/1921 |
| JP | 2-500521 A | 2/1990 |
| JP | H04-25755 U | 2/1992 |
| JP | H-6-5800 Y2 | 2/1994 |
| JP | 6-506672 A | 7/1994 |
| JP | 6-329542 A | 11/1994 |
| JP | 8-117326 A | 5/1996 |
| JP | 11-309217 A | 11/1999 |
| JP | 2000-507630 A | 6/2000 |
| JP | 2001-506144 A | 5/2001 |
| JP | 2001-520188 A | 10/2001 |
| WO | WO-89/00839 A1 | 2/1989 |
| WO | WO-96/39098 A1 | 12/1996 |
| WO | WO-97/36949 A1 | 10/1997 |
| WO | WO-99/20261 A2 | 4/1999 |
| WO | WO-99/20261 A3 | 4/1999 |
| WO | WO-01/02024 A1 | 1/2001 |

(56) References Cited

FOREIGN PATENT DOCUMENTS

| | | |
|---|---|---|
| WO | WO-01/02024 C1 | 1/2001 |
| WO | WO-01/26658 A2 | 4/2001 |
| WO | WO-01/26658 A3 | 4/2001 |
| WO | WO-01/30411 A1 | 5/2001 |
| WO | WO-01/95834 A1 | 12/2001 |
| WO | WO-03/090818 A2 | 11/2003 |
| WO | WO-03/090818 A3 | 11/2003 |
| WO | WO-03/099359 A1 | 12/2003 |
| WO | WO-2004/016200 A1 | 2/2004 |
| WO | WO-2004/082525 A2 | 9/2004 |
| WO | WO-2004/082525 A3 | 9/2004 |
| WO | WO-2006/020180 A2 | 2/2006 |
| WO | WO-2006/020180 A3 | 2/2006 |
| WO | WO-2006/107957 A2 | 10/2006 |
| WO | WO-2006/107957 A3 | 10/2006 |
| WO | WO-2007/060972 A2 | 5/2007 |
| WO | WO-2007/060972 A3 | 5/2007 |
| WO | WO-2007/067451 A2 | 6/2007 |
| WO | WO-2007/067451 A3 | 6/2007 |
| WO | WO-2007/094004 A2 | 8/2007 |
| WO | WO-2007/094004 A3 | 8/2007 |
| WO | WO-2007/113586 A1 | 10/2007 |
| WO | WO-2007/134215 A2 | 11/2007 |
| WO | WO-2007/134215 A3 | 11/2007 |
| WO | WO-2007/139668 A2 | 12/2007 |
| WO | WO-2007/139668 A3 | 12/2007 |
| WO | WO-2008/008389 A2 | 1/2008 |
| WO | WO-2008/008389 A3 | 1/2008 |
| WO | WO-2008/025156 A1 | 3/2008 |
| WO | WO-2008/033533 A2 | 3/2008 |
| WO | WO-2008/033533 A3 | 3/2008 |
| WO | WO-2008/051453 A2 | 5/2008 |
| WO | WO-2008/051453 A3 | 5/2008 |
| WO | WO-2008/051881 A2 | 5/2008 |
| WO | WO-2008/051881 A3 | 5/2008 |
| WO | WO-2008/054655 A2 | 5/2008 |
| WO | WO-2008/054655 A3 | 5/2008 |
| WO | WO-2008/070996 A1 | 6/2008 |
| WO | WO-2008/154143 A2 | 12/2008 |
| WO | WO-2008/154143 A3 | 12/2008 |
| WO | WO-2009/079418 A2 | 6/2009 |
| WO | WO-2009/079418 A3 | 6/2009 |
| WO | WO-2010/014834 A1 | 2/2010 |
| WO | WO-2010/130297 A1 | 11/2010 |
| WO | WO-2010/132648 A1 | 11/2010 |
| WO | WO-2012/083594 A1 | 6/2012 |
| WO | WO-2012/107229 A1 | 8/2012 |
| WO | WO-2012/150290 A1 | 11/2012 |
| WO | WO-2013/158337 A1 | 10/2013 |
| WO | WO-2014/151963 A1 | 9/2014 |

OTHER PUBLICATIONS

Eberhart, R.C. et al. (2003). "Bioresorbable Polymeric Stents: Current Status and Future Promise," *J. Biomater. Sci. Polymer Edn.* 14(4):299-312.
Hietala, E-M. et al. (2001). "Biodegradation of the Copolymeric Polylactide Stent," *Journal of Vascular Research* 38:361-369.
Hosemann, W. et al. (Mar. 2003, e-pub. Oct. 10, 2002). "Innovative Frontal Sinus Stent Acting as a Local Drug-Releasing System," *Eur. Arch. Otorhinolarynol.* 260:131-134.
Laaksovirta, S. (Aug. 22, 2003). *Biodegradable, Self-Reinforced, Self-Expandable Lactic and Glycolic Acid (SR-PLGA 80/20) Copolymer Spiral Prostatic Stent: Analysis of Mechanical and Biological Properties and Clinical Results,* Academic Dissertation, Medical School of the University of Tampere, 79 pages.
Lapchenko, A.S. et al. (Jun. 1996). "Polyphosphazene Prosthesis of the Frontonasal Bypass in Surgical Treatment of Acute and Chronic Inflammation of the Frontal Sinuses," *Vestnik Otorinolarinologii,* 2 pages.
Lavigne, F. et al. (May 2002). "Intrasinus Administration of Topical Budesonide to Allergic Patients With Chronic Rhinosinusitis Following Surgery," *The Laryngoscope* 112, 7 pages.
Min, Y-G. et al. (1995). "Application of Polylactic Acid Polymer in the Treatment of Acute Maxillary Sinusitis in Rabbits," *Acta Otolaryngol.* 115:548-552.
Min, Y-G. et al. (Aug. 1995). "Mucociliary Activity and Histopathology of Sinus Mucosa in Experimental Maxillary Sinusitis: A Comparison of Systemic Administration of Antibiotic and Antibiotic Delivery by Polylactic Acid Polymer," *The Laryngoscope* 105:835-842.
Murphy, J.G. et al. (1992). "Percutaneous Polymeric Stents in Porcine Coronary Arteries: Initial Experience With Polyethylene Terephthalate Stents," *Circulation* 86:1596-1604.
Nguyen, K.T. et al. (2004). "Biomaterials and Stent Technology," Chapter 5 in *Tissue Engineering and Novel Delivery Systems,* 24 pages.
Nuutinen, J-P. et al. (2002). "Mechanical Properties and in vitro Degradation of Bioresorbable Knitted Stents," *J. Biomater. Sci. Polymer Edn.* 13(12):1313-1323.
Nuutinen, J-P. et al. (2003). "Theoretical and Experimental Evaluation of the Radial Force of Self-Expanding Braided Bioabsorbable Stents," *J. Biomater. Sci. Polymer Edn.* 14(7):677-687.
Parviainen, M. et al. (2000). "A New Biodegradable Stent for the Pancreaticojejunal Anastomosis After Pancreaticoduodenal Resection: In Vitro Examination and Pilot Experiences in Humans," *Pancreas* 21(1):14-21.
Piskunov, S.Z. et al. (May-Jun. 1989). "Application of Drugs Based on Polymers in the Treatment of Acute and Chronic Maxillary Sinusitis," *Vestnik Otorinolaringologii* (3)33-35.
Piskunov, S. et al. (1993). "The Prolongation of Drug Action in the Treatment of Diseases of the Nose and Paranasal Sinuses," *Rhinology* 31:33-36.
Roumestan, C. et al. (2003). "Fluticasone Propionate and Mometasone Furoate Have Equivalent Transcriptional Potencies," *Clinical and Experimental Allergy* 33:895-901.
Shikani, A.H. (Aug. 1996). "Use of Antibiotics for Expansion of the Merocel® Packing Following Endoscopic Sinus Surgery," *ENT-Ear, Nose & Throat Journal* 75(8):524-528.
St. Croix, B. et al. (Aug. 18, 2000). "Gene Expressed in Human Tumor Endothelium," *Science* 289:1197-1202.
Su, S-H. et al. (2003). "Expandable Bioresorbable Endovascular Stent. I. Fabrication and Properties," *Annals of Biomedical Engineering* 31:667-677.
Tamai, H. et al. (1999). "A Biodegradable Ploy-/-lactic Acid Coronary Stent in the Porcine Coronary Artery," *Journal of Interventional Cardiology* 12(6):443-450.
Thierry, B. et al. (Nov./Dec. 2003, e-pub. Oct. 7, 2003). "Bioactive Coatings of Endovascular Stents Based on Polyelectrolyte Multilayers," *Biomacromolecules* 4(6):1564-1571.
Toffel, P.H. (Mar. 2001). "The Balanced Philosophy of Secure Multimodal Endoscopic Sinus Surgery with Adjunct Use of Middle Meatal Stenting and Middle Turbinate Modification," *Operative Techniques in Otolaryngology—Head and Neck Surgery* 12(1):40-45.
Vogt, F. et al. (2004, e-pub. Jul. 20, 2004). "Long-Term Assessment of a Novel Biodegradable Paclitaxel-Eluting Coronary Polylactide Stent," *European Heart Journal* 25:1330-1340.
European Search Report dated Sep. 25, 2012 for European Patent Application No. 10775524.1, filed May 13, 2010, 9 pages.
Extended European Search Report and European Search Opinion dated Jun. 27, 2014, for European Patent Application No. 14156004.5, filed May 13, 2010, 13 pages.
International Search Report dated Jul. 16, 2010 for PCT Patent Application No. PCT/US2010/034679, filed May 13, 2010, 2 pages.
Written Opinion dated Jul. 16, 2010, for PCT Patent Application No. PCT/US2010/034679, filed May 13, 2010, 4 pages.
International Search Report dated Oct. 9, 2014, for PCT Application No. PCT/US2014/026737, filed Mar. 13, 2014, 5 pages.
Written Opinion dated Oct. 9, 2014, for PCT Application No. PCT/US2014/026737, filed Mar. 13, 2014, 5 pages.
Final Office Action dated Jan. 8, 2009, for U.S. Appl. No. 10/800,162, filed Mar. 12, 2004, 5 pages.
Final Office Action dated Jul. 22, 2009, for U.S. Appl. No 11/398,342, filed Apr. 4, 2006, 8 pages.

(56) References Cited

OTHER PUBLICATIONS

Final Office Action dated Jul. 8, 2010, for U.S. Appl. No. 11/398,342, filed Apr. 4, 2006, 7 pages.
Final Office Action dated Aug. 18, 2010, for U.S. Appl. No. 11/775,157, filed Jul. 9, 2007, 12 pages.
Final Office Action dated Jan. 27, 2011, for U.S. Appl. No. 12/479,794, filed Jun. 6, 2009, 6 pages.
Final Office Action dated Nov. 28, 2011, for U.S. Appl. No. 12/883,071, filed Sep. 15, 2010, 7 pages.
Final Office Action dated Mar. 1, 2012, for U.S. Appl. No. 12/270,695, filed Nov. 13, 2008, 26 pages.
Final Office Action dated Apr. 12, 2012, for U.S. Appl. No. 12/883,087, filed Sep. 15, 2010, 7 pages.
Final Office Action dated Apr. 16, 2012, for U.S. Appl. No. 12/334,373, filed Dec. 12, 2008, 7 pages.
Final Office Action dated May 29, 2012, for U.S. Appl. No. 12/334,382, filed Dec. 12, 2008, 7 pages.
Final Office Action dated Mar. 6, 2013, for U.S. Appl. No. 13/341,732, filed Dec. 30, 2011, 7 pages.
Final Office Action dated May 30, 2013, for U.S. Appl. No. 12/541,840, filed Aug. 14, 2009, 11 pages.
Final Office Action dated Sep. 10, 2013, for U.S. Appl. No. 12/334,395, filed Dec. 12, 2008, 8 pages.
Final Office Action dated Dec. 2, 2013, for U.S. Appl. No. 12/779,240, filed May 13, 2010, 10 pages.
Final Office Action dated May 5, 2014 for U.S. Appl. No. 12/883,087, filed Sep. 15, 2010, 10 pages.
Final Office Action dated May 19, 2014, for U.S. Appl. No. 13/341,732, filed Dec. 30, 2011, 7 pages.
Final Office Action dated Sep. 17, 2014, for U.S. Appl. No. 12/334,395, filed Dec. 12, 2008, 11 pages.
Non-Final Office Action dated Jun. 6, 2008, for U.S. Appl. No. 10/800,162, filed Mar. 12, 2004, 5 pages.
Non-Final Office Action dated Nov. 25, 2008, for U.S. Appl. No. 11/398,342, filed Apr. 4, 2006, 10 pages.
Non-Final Office Action dated Sep. 22, 2009, for U.S. Appl. No. 12/419,927, filed Apr. 7, 2009, 4 pages.
Non-Final Office Action dated Sep. 22, 2009, for U.S. Appl. No. 12/419,943, filed Apr. 7, 2009, 5 pages.
Non-Final Office Action dated Sep. 22, 2009, for U.S. Appl. No. 12/419,930, filed Apr. 7, 2007, 4 pages.
Non-Final Office Action dated Sep. 22, 2009, for U.S. Appl. No. 12/419,937, filed Apr. 7, 2009, 4 pages.
Non-Final Office Action dated Sep. 22, 2009, for U.S. Appl. No. 12/419,925, filed Apr. 7, 2009, 4 pages.
Non-Final Office Action dated Nov. 13, 2009, for U.S. Appl. No. 11/398,342, filed Apr. 4, 2006, 9 pages.
Non-Final Office Action dated Dec. 9, 2009, for U.S. Appl. No. 11/775,157, filed Jul. 9, 2007, 12 pages.
Non-Final Office Action dated Jul. 1, 2010, for U.S. Appl. No. 12/479,794, filed Jun. 6, 2009, 5 pages.
Non-Final Office Action dated Sep. 10, 2010, for U.S. Appl. No. 12/437,374, filed May 7, 2009, 8 pages.
Non-Final Office Action dated Nov. 12, 2010, for U.S. Appl. No. 11/398,342, filed Apr. 4, 2006, 8 pages.
Non-Final Office Action dated Nov. 23, 2010, for U.S. Appl. No. 12/258,277, filed Oct. 24, 2008, 9 pages.
Non-Final Office Action dated Nov. 23, 2010, for U.S. Appl. No. 12/258,282, filed Oct. 24, 2008, 7 pages.
Non-Final Office Action dated Nov. 24, 2010, for U.S. Appl. No. 12/883,090, filed Sep. 15, 2010, 7 pages.
Non-Final Office Action dated Nov. 24, 2010, for U.S. Appl. No. 12/883,056, filed Sep. 15, 2010, 7 pages.
Non-Final Office Action dated Nov. 24, 2010, for U.S. Appl. No. 12/883,079, filed Sep. 15, 2010, 8 pages.
Non-Final Office Action dated Mar. 22, 2011, for U.S. Appl. No. 12/883,071, filed Sep. 15, 2010, 8 pages.
Non-Final Office Action dated May 13, 2011, for U.S. Appl. No. 12/883,087, filed Sep. 15, 2010, 7 pages.
Non-Final Office Action dated Jun. 14, 2011, for U.S. Appl. No. 12/437,374, filed May 7, 2009, 8 pages.
Non-Final Office Action dated Jun. 21, 2011, for U.S. Appl. No. 12/270,695, filed Nov. 13, 2008, 24 pages.
Non-Final Office Action dated Jul. 13, 2011, for U.S. Appl. No. 12/334,373, filed Dec. 12, 2008, 8 pages.
Non-Final Office Action dated Sep. 26, 2011, for U.S. Appl. No. 12/334,382, filed Dec. 12, 2008, 7 pages.
Non-Final Office Action dated May 11, 2012, for U.S. Appl. No. 12/883,071, filed Sep. 15, 2010, 7 pages.
Non-Final Office Action dated May 14, 2012, for U.S. Appl. No. 12/779,240, filed May 13, 2010, 9 pages.
Non-Final Office Action dated Jun. 7, 2012, for U.S. Appl. No. 12/334,395, filed Dec. 12, 2008, 7 pages.
Non-Final Office Action dated Oct. 18, 2012, for U.S. Appl. No. 12/541,840, filed Aug. 14, 2009, 10 pages.
Non-Final Office Action dated Mar. 15, 2013, for U.S. Appl. No. 12/512,855, filed Jul. 30, 2009, 10 pages.
Non-Final Office Action dated Sep. 12, 2013 for U.S. Appl. No. 13/341,732, filed Dec. 30, 2011, 5 pages.
Non-Final Office Action dated Sep. 23, 2013, for U.S. Appl. No. 12/883,087, filed Sep. 15, 2010, 7 pages.
Non-Final Office Action dated Feb. 27, 2014, for U.S. Appl. No. 12/270,695, filed Nov. 13, 2008, 7 pages.
Non-Final Office Action dated Apr. 16, 2014, for U.S. Appl. No. 12/334,395, filed Dec. 12, 2008, 9 pages.
Non-Final Office Action dated Jun. 12, 2014, for U.S. Appl. No. 14/082,010, filed Nov. 15, 2013, 6 pages.
Non-Final Office Action dated Sep. 23, 2014, for U.S. Appl. No. 13/341,732, filed Dec. 30, 2011, 13 pages.
Notice of Allowance dated Dec. 23, 2009, for U.S. Appl. No. 12/419,925, filed Apr. 7, 2009, 2 pages.
Notice of Allowance dated Dec. 23, 2009, for U.S. Appl. No. 12/419,943, filed Apr. 7, 2009, 2 pages.
Notice of Allowance dated Dec. 24, 2009, for U.S. Appl. No. 12/419,927, filed Apr. 7, 2009, 2 pages.
Notice of Allowance dated Jan. 19, 2010, for U.S. Appl. No. 12/419,930, filed Apr. 7, 2009, 2 pages.
Notice of Allowance dated Feb. 2, 2010, for U.S. Appl. No. 12/419,937, filed Apr. 7, 2009, 2 pages.
Notice of Allowance dated Mar. 18, 2011, for U.S. Appl. No. 12/258,277, filed Oct. 24, 2008, 7 pages.
Notice of Allowance dated Mar. 21, 2011, for U.S. Appl. No. 12/258,282, filed Oct. 24, 2008, 8 pages.
Notice of Allowance dated Mar. 21, 2011, for U.S. Appl. No. 12/883,059, filed Sep. 15, 2010, 10 pages.
Notice of Allowance dated Mar. 23, 2011, for U.S. Appl. No. 12/883,079, filed Sep. 15, 2010, 9 pages.
Notice of Allowance dated Mar. 25, 2011 for U.S. Appl. No. 12/883,090, filed Sep. 15, 2010, 8 pages.
Notice of Allowance dated Mar. 25, 2011, for U.S. Appl. No. 12/883,056, filed Sep. 15, 2010, 8 pages.
Notice of Allowance dated Jul. 13, 2011, for U.S. Appl. No. 11/398,342, filed Apr. 4, 2006, 7 pages.
Notice of Allowance dated Nov. 9, 2011, for U.S. Appl. No. 12/479,794, filed Jun. 6, 2009, 7 pages.
Notice of Allowance dated Aug. 20, 2012, for U.S. Appl. No. 12/437,374, filed May 7, 2009, 8 pages.
Notice of Allowance dated Nov. 2, 2012, for U.S. Appl. No. 11/775,157, filed Jul. 9, 2007, 8 pages.
Notice of Allowance dated May 22, 2013, for U.S. Appl. No. 11/775,157, filed Jul. 9, 2007, 10 pages.
Notice of Allowance dated Jul. 15, 2013, for U.S. Appl. No. 12,334,382, filed Dec. 12, 2008, 9 pages.
Notice of Allowance dated Jul. 30, 2013, for U.S. Appl. No. 12/334,373, filed Dec. 12, 2008, 10 pages.
Notice of Allowance dated Sep. 19, 2013, for U.S. Appl. No. 12/883,071, filed Sep. 15, 2010, 6 pages.
Notice of Allowance dated Nov. 27, 2013, for U.S. Appl. No. 12/512,855, filed Jul. 30, 2009, 9 pages.
Notice of Allowance dated Jan. 21, 2014, for U.S. Appl. No. 12/883,071, filed Sep. 15, 2010, 6 pages.

(56) References Cited

OTHER PUBLICATIONS

Notice of Allowance dated Feb. 19, 2014, for U.S. Appl. No. 12/512,855, filed Jul. 30, 2009, 7 pages.
Notice of Allowance dated Apr. 8, 2014, for U.S. Appl. No. 12/541,840, filed Aug. 14, 2009, 8 pages.
Notice of Allowance (Corrected) dated May 29, 2014, for U.S. Appl. No. 12/512,855, filed Jul. 30, 2009, 4 pages.
Notice of Allowance dated Jun. 12, 2014, for U.S. Appl. No. 12/270,695, filed Nov. 13, 2008, 7 pages.
Third Party Submission under 37 CFR 1.290 submitted Oct. 11, 2014, against U.S. Appl. No. 14/081,974, filed Nov. 15, 2013 (8 pages).
European Office Action dated Mar. 10, 2015, for European Patent Application No. 10011118.6, filed on Sep. 28, 2010, 5 pages.
European Office Action dated Mar. 6, 2015, for European Patent Application No. 10011116.0, filed on Sep. 28, 2010, 4 pages.
European Office Action dated Mar. 6, 2015, for European Patent Application No. 10011117.8, filed on Sep. 28, 2010, 4 pages.
Final Office Action dated Feb. 12, 2015, for U.S. Appl. No. 13/341,732, filed Dec. 30, 2011, 8 pages.
Non-Final Office Action dated Apr. 28, 2015, for U.S. Appl. No. 12/779,240, filed Apr. 130, 2010, 12 pages.
Non-Final Office Action dated Mar. 20, 2015, for U.S. Appl. No. 12/883,087, filed Sep. 15, 2010, 11 pages.
Bolliger, C.T. et al. (1999). "Evaluation of a New Self-Expandable Silicone Stent in an Experimental Tracheal Stenosis," *Chest* 115:496-501.
European Office Action dated May 8, 2015, for EP Patent Application No. 06 749 235.5, filed on Apr. 4, 2006, 4 pages.
European Search Report dated Feb. 21, 2011, for EP Patent Application No. 10011116.0 filed on Apr. 4, 2006, 8 pages.
European Search Report dated Feb. 21, 2011, for EP Patent Application No. 10011117.8 filed on Apr. 4, 2006, 8 pages.
European Search Report dated Feb. 21, 2011, for EP Patent Application No. 10011118.6 filed on Apr. 4, 2006, 8 pages.
Final Office Action dated Oct. 20, 2015, for U.S. Appl. No. 12/883,087, filed Sep. 15, 2010, 15 pages.
Final Office Action dated Nov. 25, 2015, for U.S. Appl. No. 12/779,240, filed May 13, 2010, 15 pages.
Hughes, J.P. et al. (Apr. 2004). "Use of a Ureteric Pigtail Stent as a Self-Retaining Frontal Sinus Stent," *The Journal of Laryngology & Otology* 118:299-301.
International Search Report dated Feb. 24, 2006, for PCT Application No. PCT/US04/07828, filed Mar. 12, 2004, 1 page.
International Search Report dated Sep. 11, 2006, for PCT Patent Application No. PCT/US2006/012484 filed on Apr. 4, 2006, 6 pages.
International Search Report dated Mar. 19, 2008, for PCT Patent Application No. PCT/US2007/015813, filed on Jul. 10, 2007, 3 pages.
International Search Report dated Apr. 16, 2009, for PCT Application No. PCT/US2008/86178, filed on Dec. 12, 2008, 5 pages.
International Search Report dated Sep. 28, 2009, for PCT Application No. PCT/US2009/052287, filed on Jul. 30, 2009, 2 pages.
Mirza, S. et al. (Dec. 2000). "A Simple and Effective Frontal Sinus Stent," *The Journal of Laryngology & Otology* 114:955-956.
Mitty, H. et al. (1988). "Experience with a New Ureteral Stent Made of a Biocompatible Copolymer," *Radiology* 168:557-559.
Non-Final Office Action dated May 8, 2015, for U.S. Appl. No. 12/334,395, filed Dec. 12, 2008, 11 pages.
Non-Final Office Action dated Aug. 6, 2015, for U.S. Appl. No. 14/327,100, filed Jul. 7, 2014, 6 pages.
Non-Final Office Action dated Sep. 10, 2015, for U.S. Appl. No. 13/341,732, filed Dec. 30, 2011, 6 pages.
Non-Final Office Action dated Nov. 12, 2015, for U.S. Appl. No. 14/327,100, filed Jul. 9, 2014, 12 pages.
Corrected Notice of Allowance dated Feb. 17, 2015, for U.S. Appl. No. 14/082,010, filed Nov. 15, 2013, 5 pages.
Restriction Requirement dated Aug. 6, 2015, for U.S. Appl. No. 14/327,100, filed Jul. 7, 2014, 6 pages.

Supplementary European Search Report and Search Opinion dated Nov. 9, 2010, for European Patent Application No. 04720509.1, filed on Mar. 12, 2004, 3 pages.
Supplementary European Search Report and Search Opinion dated Jun. 26, 2015, for European Patent Application No. 09803604.9, filed on Jul. 30, 2009, 7 pages.
Extended European Search Report dated Jan. 27, 2017, for EP Application No. 14 770 721.0, filed on Mar. 13, 2014, 10 pages.
Extended European Search Report dated Nov. 16, 2016, for EP Application No. 16 165 633.5, filed on May 13, 2010, 9 pages.
Extended European Search Report dated Jun. 18, 2015, for EP Patent Application No. 08 863 327.6, filed on Jul. 16, 2010, 8 pages.
Extended European Search Report dated Jun. 26, 2015, for European Patent Application No. 09 803 604.9, filed on Jul. 30, 2009, 7 pages.
Final Office Action dated Feb. 8, 2016, for U.S. Appl. No. 12/334,395, filed Dec. 12, 2008, 18 pages.
Final Office Action dated Jun. 29, 2016, for U.S. Appl. No. 14/327,100, filed Jul. 9, 2014, 17 pages.
Final Office Action dated Sep. 16, 2016, for U.S. Appl. No. 14/081,974, filed Nov. 15, 2013, 12 pages.
Final Office Action dated Sep. 20, 2016, for U.S. Appl. No. 14/550,634, filed Nov. 21, 2014, 11 pages.
Non-Final Office Action dated Nov. 18, 2016, for U.S. Appl. No. 12/779,240, filed May 13, 2010, 15 pages.
Non-Final Office Action dated Feb. 5, 2016, for U.S. Appl. No. 12/883,087, filed Sep. 15, 2010, 12 pages.
Non-Final Office Action dated Feb. 5, 2016, for U.S. Appl. No. 14/081,974, filed Nov. 15, 2013, 12 pages.
Non-Final Office Action dated Apr. 28, 2016, for U.S. Appl. No. 14/550,634, filed Nov. 21, 2014, 10 pages.
Non-Final Office Action dated Aug. 11, 2016, for U.S. Appl. No. 12/334,395, filed Dec. 12, 2008, 12 pages.
Notice of Allowance dated Dec. 23, 2009, for U.S. Appl. No. 12/419,925, filed Apr. 7, 2009, 4 pages.
Notice of Allowance dated Nov. 12, 2014, for U.S. Appl. No. 14/082,010, filed Nov. 15, 2013, 5 pages.
Notice of Allowance dated Nov. 18, 2016, for U.S. Appl. No. 14/298,715, filed Jun. 6, 2014, 8 pages.
Partial Supplementary European Search Report dated Oct. 27, 2016, for EP Application No. 14 770 721.0, filed Mar. 13, 2014, 6 pages.
Written Opinion of the International Searching Authority dated Feb. 24, 2006 for PCT Application No. PCT/US04/07828, filed Mar. 12, 2004, 3 pages.
Written Opinion of the International Searching Authority dated Sep. 11, 2006, for PCT Patent Application No. PCT/US2006/012484, filed on Apr. 4, 2006, 11 pages.
Written Opinion of the International Searching Authority dated Mar. 19, 2008, for PCT Patent Application No. PCT/US2007/015813, filed on Jul. 10, 2007, 7 pages.
Written Opinion of the International Searching Authority dated Apr. 16, 2009, for PCT Application No. PCT/US2008/86718, filed on Dec. 12, 2008, 13 pages.
Written Opinion of the International Searching Authority dated Sep. 28, 2009, for PCT Application No. PCT/US2009/052287, filed on Jul. 30, 2009, 9 pages.
Final Office Action dated Jul. 26, 2017, 2017, for U.S. Appl. No. 12/779,240, filed May 13, 2010, 13 pages.
Non-Final Office Action dated Apr. 16, 2018, for U.S. Appl. No. 15/007,848, filed Jan. 27, 2016, 7 pages.
Non-Final Office Action dated Jul. 25, 2018, for U.S. Appl. No. 12/779,240, filed May 13, 2010, 14 pages.
Corrected Notice of Allowability dated Jan. 24, 2019, for U.S. Appl. No. 15/007,848, filed Jan. 27, 2016, 2 pages.
Notice of Allowance dated Dec. 20, 2018, for U.S. Appl. No. 15/007,848, filed Jan. 27, 2016, 8 pages.
Notice of Allowance dated Mar. 7, 2019, for U.S. Appl. No. 12/779,240, filed May 13, 2010, 11 pages.
Corrected Notice of Allowabiiity dated Apr. 16, 2019, for U.S. Appl. No. 12/779,240, filed May 13, 2010, 4 pages.

(56) References Cited

OTHER PUBLICATIONS

Corrected Notice of Allowability dated Mar. 25, 2019, for U.S. Appl. No. 12/779,240, filed May 13, 2010, 6 pages.

* cited by examiner

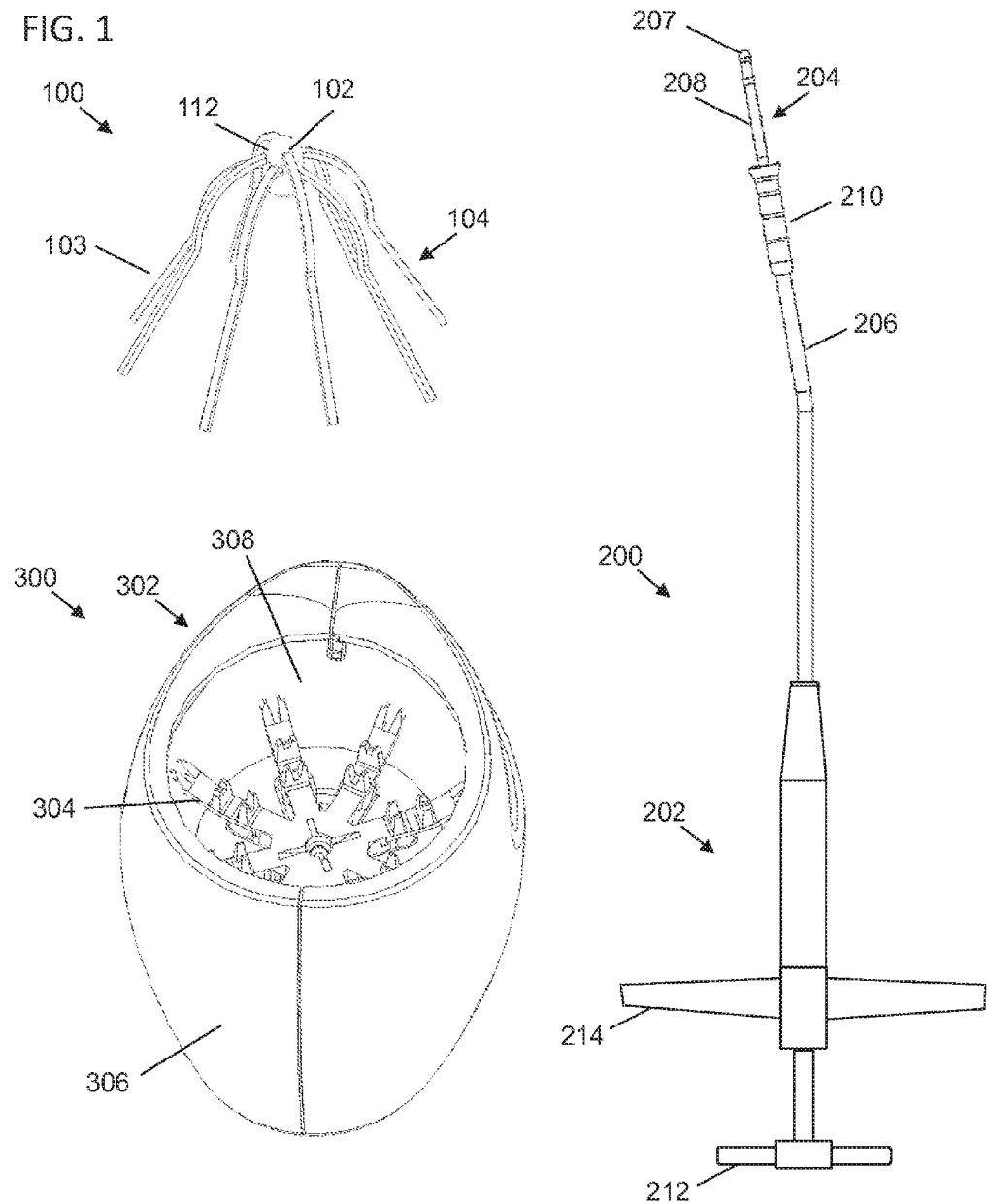

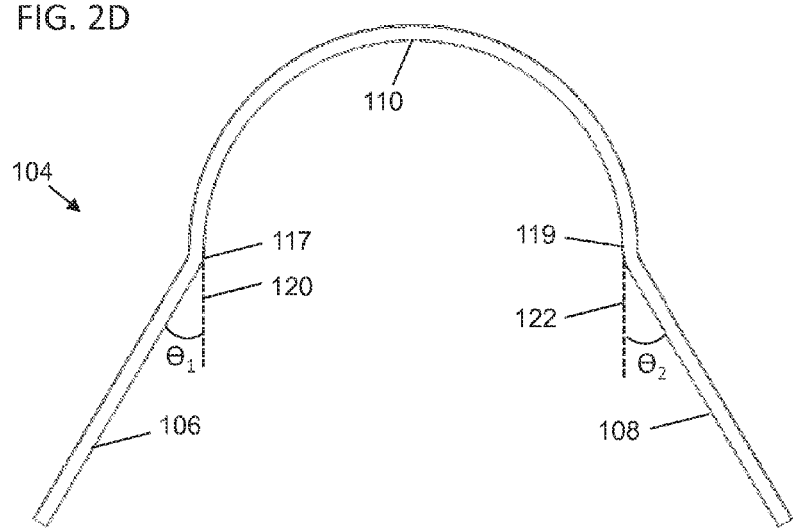
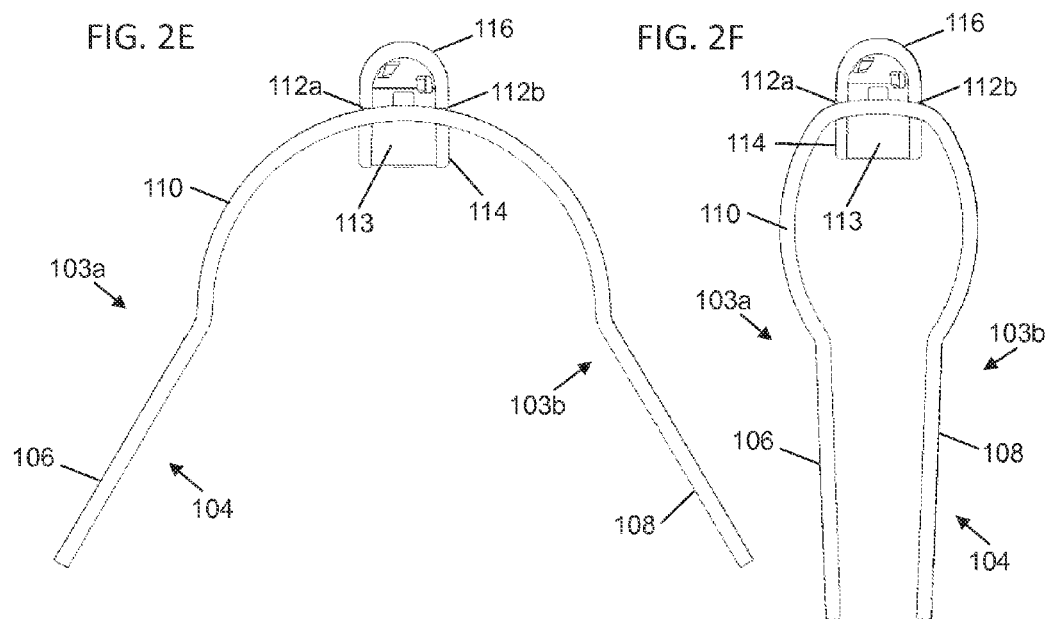

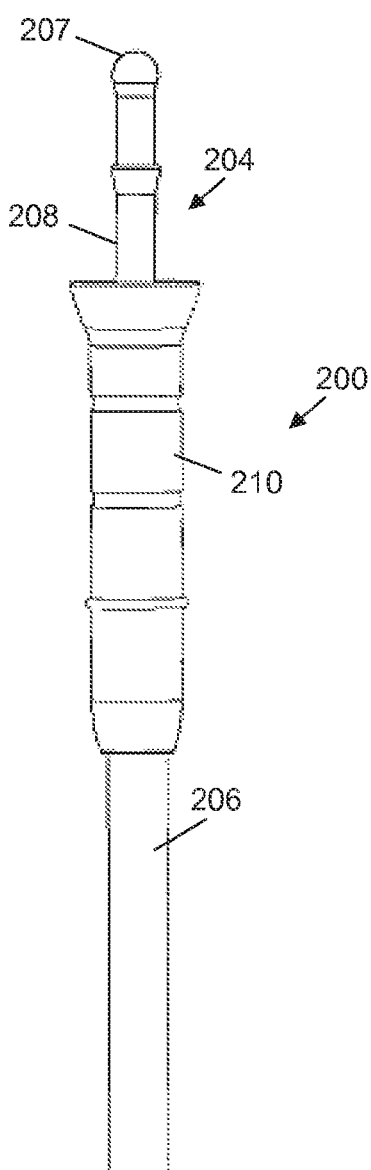
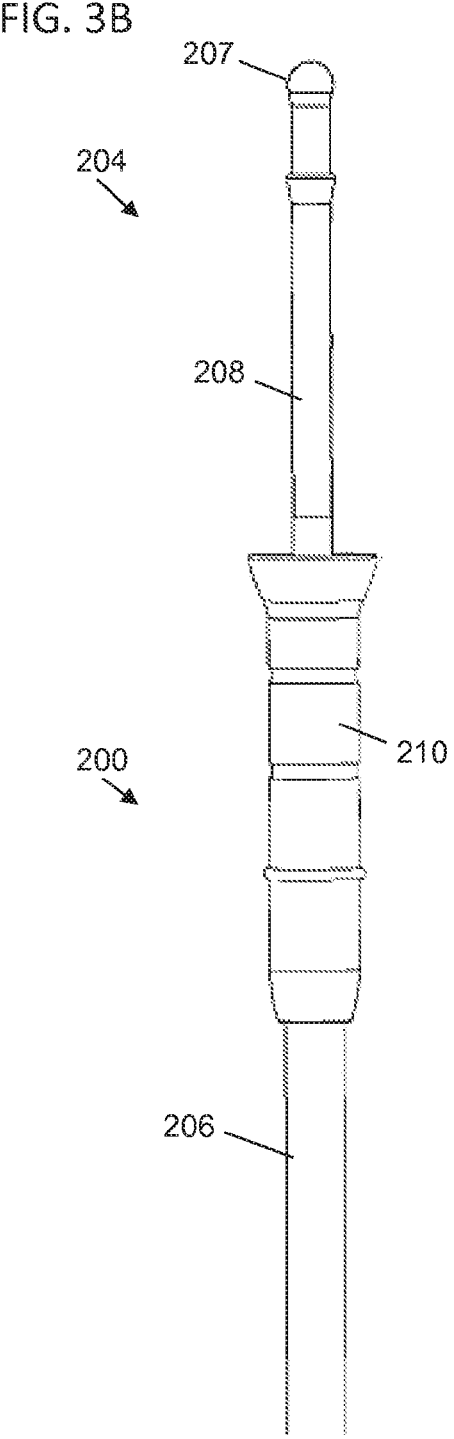
FIG. 3A
FIG. 3B

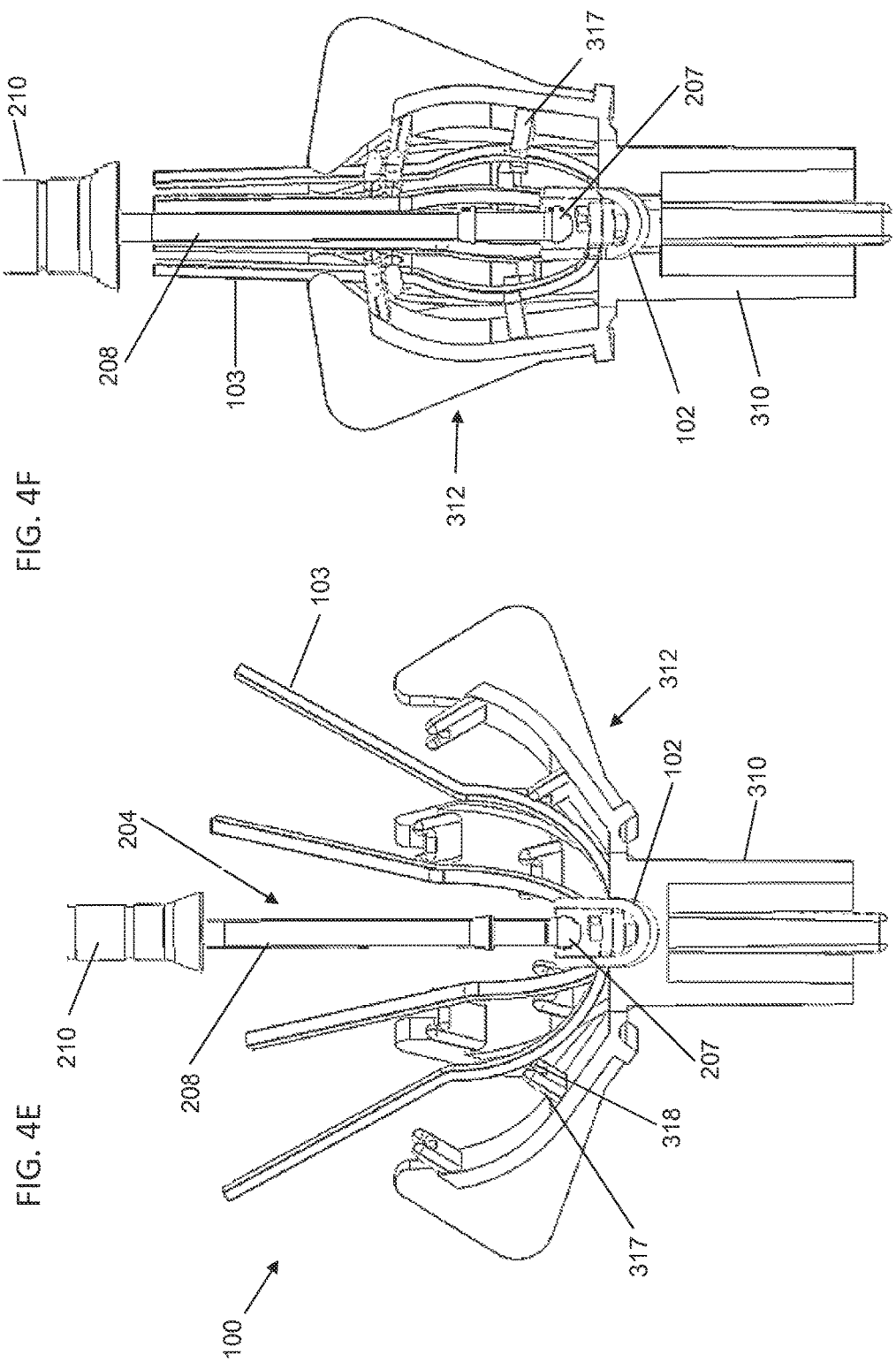

SYSTEMS, DEVICES, AND METHOD FOR TREATING A SINUS CONDITION

CROSS-REFERENCE TO RELATED APPLICATIONS

This application claims priority to U.S. Provisional Application Ser. No. 61/785,939, filed on Mar. 14, 2013, and titled "SYSTEMS, DEVICES, AND METHOD FOR TREATING A SINUS CONDITION," the content of which is hereby incorporated in its entirety.

FIELD

The invention is generally related to expandable implants, devices for delivering and/or crimping implants, and methods of using them.

BACKGROUND

There is a movement toward using minimally-invasive approaches to treat conditions or diseases associated with bodily structures such as the nasal passageways, sinus cavities, or the like. For example, individuals suffering from nasal polyposis may have obstructed airways or sinus ostia, and may experience symptoms such as difficulty breathing, headaches, sneezing, snoring, and general discomfort. Expandable implants may be useful in maintaining, opening, or dilating bodily structures such as nasal passageways, paranasal sinus cavities, or the like. Given the variety of benefits that these devices may provide, additional expandable devices may be desirable, as well as systems for crimping and/or delivering such implants.

BRIEF SUMMARY

Described here are devices, systems, and methods for treating one or more sinus or nasal conditions. Also described here are devices and methods for crimping an implant. In some variations, the devices may comprise an expandable implant comprising a hub and plurality of filaments. The hub may comprise a plurality of apertures extending through the hub, and each filament of the plurality of filaments may be positioned in a corresponding aperture to extend through the hub. In these variations, placement of a filament in a corresponding aperture may define a first leg on a first side of the hub and a second leg on the second side of the hub. In some variations, the filament may comprise a first straight segment, a second straight segment, and a curved segment positioned between the first straight segment and the second straight segment. In some of these variations, the curved segment of each filament may be positioned in the corresponding aperture to position the first straight segment on the first side of the hub and the second straight segment on the second side of the hub. In some variations, each filament may be an extruded polymer filament. In some variations, the hub and the plurality of filaments may be formed from one or more biodegradable materials. In some variations, the implant may comprise a drug-releasing coating. The implants described here may be delivered to any suitable location, such as a sinus or nasal cavity. In some variations, the methods described here may comprise advancing an implant to a location in a sinus cavity, sinus ostium, or nasal passageway, delivering the implant, and expanding the implant from a low-profile configuration to an expanded configuration.

Described here are methods for crimping an implant. In some variations, the device may comprise a housing and a crimping member. The crimping member may comprise a plurality of arms radially extending from a stem portion, and the housing may comprise a recess, such that movement of the stem portion into the recess may rotate the plurality of arms relative to the stem portion. In some variations, the recess may comprise a central recess and a plurality of channels radially extending from the central recess. In some of these variations, each arm of the plurality of arms may be at least partially positioned within a corresponding channel of the plurality of channels. In some variations, the device may further comprise a spring positioned between the stem portion and the recess. Additionally or alternatively, each arm of the plurality of arms may comprise at least one holder having a channel. In some variations the stem portion may comprise a recess configured to receive a portion of the implant.

Also described here are systems for treating a patient comprising an implant and a crimping device. The implant may comprise a plurality of legs, and in some instances may further comprise a hub attaching the plurality of legs. The crimping device may comprise a crimping member, which may be configured to engage the plurality of legs and move the implant to a low-profile configuration. In some instances, each leg of an implant may be engaged by a correspond arm of a crimping member of the crimping device. The crimping member may be moved into a recess of a housing of the crimping member to rotate the plurality of arms relative to a stem portion of the crimping device. This rotation of the arms may rotate the corresponding legs of the implant to move the implant to a low-profile configuration. In some variations, a delivery device may be used to push the crimping member into the recess of the housing. In some of these variations, a portion of the delivery device may be advanced to hold the implant in a low-profile configuration.

In some variations, a crimping device may comprise a housing, the housing defining a crimping chamber having a proximal end and distal end, the crimping chamber having a proximal opening at the proximal end of the crimping chamber. The crimping device may further comprise a plurality of ribs located within the crimping chamber, wherein the plurality of ribs defines a plurality of channels between adjacent ribs of the plurality of ribs. The crimping chamber may comprise a first segment and a second segment, wherein the first segment extends from the proximal opening to a proximal end of the second segment. In some of these variations, the first segment may have an outer diameter which tapers from a first diameter at a proximal end of the first segment to a second diameter at a distal end of the first segment, wherein the first diameter is larger than the second diameter. In some of these variations, the second segment may have an outer diameter equal to the second diameter.

In some variations, the crimping chamber may further comprise a third segment, wherein the second segment extends distally from a distal end of the second segment. In some of these variations, the third segment may have an outer diameter equal to an outer diameter of the second segment. Additionally or alternatively, the inner diameter of the second segment is equal to an outer diameter of the second segment. Additionally or alternatively, the third segment has an inner diameter smaller than an inner diameter of the second segment. In some variations the system may further comprise a delivery device having an inner shaft and an outer sheath. In some of these variations, an outer diameter of a distal end of the outer sheath may be less than or equal to the inner diameter of the second segment and greater than the inner diameter of the third segment.

In some variations, the plurality of ribs and plurality of channels extend at least partially through each of the first, second, and third segments. In other variations, the plurality of ribs and the plurality of channels may comprise a first plurality of ribs and a first plurality of channels extending at least partially through first segment and a second plurality of ribs extends and a second plurality of channels extending at least partially along the third segment. In some variations, the system may further comprise an implant, wherein the implant comprises a hub and a plurality of legs extending from the hub and wherein the implant is moveable from an expanded configuration to a low-profile configuration. The first segment and second segment may be sized such that advancement of the hub from the first segment into the second segment crimps the implant from the expanded configuration to the low-profile configuration. In some variations the crimping device may further comprise a cap removably connected to the housing. In some variations, the housing may further comprise a base.

BRIEF DESCRIPTION OF THE DRAWINGS

FIG. 1 depicts an illustrative variation of the systems described here.

FIGS. 2C and 2D depict side views of a hub and a filament, respectively, of the implant of FIGS. 2A and 2B. FIGS. 2E and 2F show cross-sectional side views of the implant of FIGS. 2A and 2B.

FIGS. 3A and 3B depict side views of a distal portion of a delivery device as described here.

FIGS. 4E and 4F depict cross-sectional side views of the crimping device of FIG. 4A in operation.

DETAILED DESCRIPTION

Described here are devices, systems, and methods for treating one or more sinus or nasal conditions with an implant. Also described here are devices and methods for crimping an implant. Generally, the systems comprise an implant sized and configured for placement in one or more portions of the paranasal sinus or nasal cavities. The implant may be delivered in a low-profile configuration, and may be expanded in the paranasal sinus or nasal cavity to dilate, separate, or otherwise press against tissue, which in some instances may assist in opening an airway of a patient. The implant may be configured to deliver or release one or more drugs (e.g., to surrounding tissue). In some variations, the systems may comprise a delivery device for delivering the implant into the body. Additionally or alternatively, the systems may comprise a crimping device configured to place the implant in a low-profile configuration.

FIG. 1 shows an illustrative variation of the systems described here. As shown there, the system may comprise an implant (100), a delivery device (200), and a crimping device (300). The implant (100) is generally moveable between a low-profile configuration and an expanded configuration, and the crimping device (300) may be configured to move the implant (100) from an expanded configuration to a low-profile configuration. The implant (100) may be releasably coupled to the delivery device (200), which may be used to advance the implant (100) in a low-profile configuration into the body. The delivery device (200) may release the implant (100) at a target location in the body (e.g., a paranasal sinus cavity, a nasal cavity, or the like), and the implant (100) may be expanded into contact with surrounding tissue. In some variations, the implant (100) may self-expand when delivered. Additionally or alternatively, a separate device (e.g., a balloon) may be used to expand the implant (100) (or, in the instances of a self-expanding implant, to aid in expansion of the implant). While the system is shown in FIG. 1 as comprising an implant (100), a delivery device (200), and a crimping device (300), it should be appreciated that the systems may comprise an implant only, may comprise an implant and a delivery device, may comprise an implant and a crimping device, or the like. Each of the implant (100), delivery device (200), and crimping device (300) will be described in more detail below.

Figure 2A:
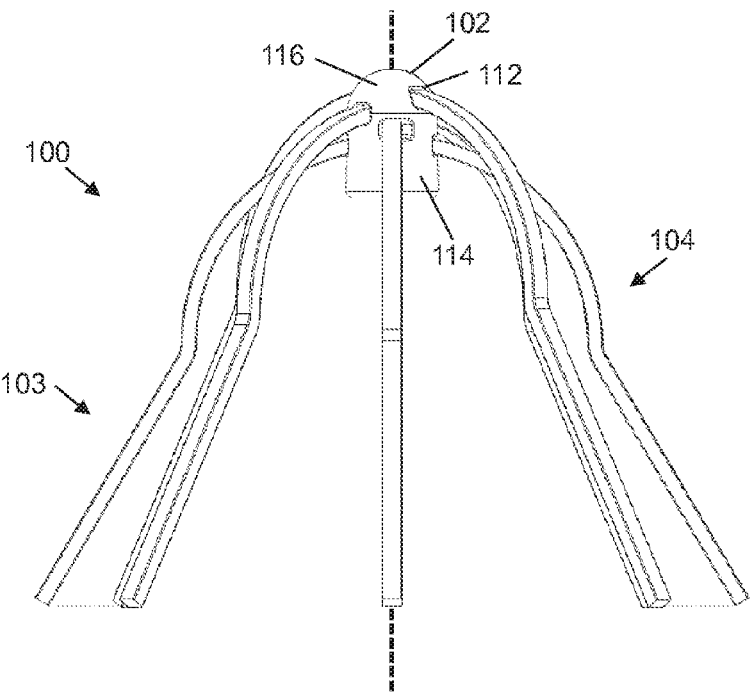
FIGS. 2A and 2B depict side views of a variation of the implants described here.
Figure 2B:
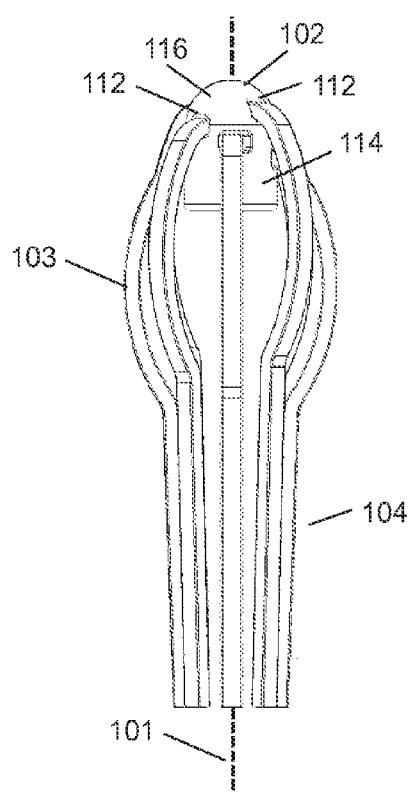

FIGS. 2A-2F depict a variation of the implant (100) shown in FIG. 1. Specifically, FIGS. 2A and 2B show side views of the implant (100). As shown there, the implant may comprise a hub (102) and a plurality of legs (103) extending from the hub (102). The legs (103) may be moveable between an expanded configuration, as shown in FIG. 2A, and a low-profile (e.g., unexpanded) configuration, as shown in a side view in FIG. 2B. Specifically, the legs (103) may rotate toward a longitudinal axis (101) of the implant (100) to move the implant toward the low-profile configuration, and may rotate away from the longitudinal axis (101) to move the implant toward an expanded configuration. In some variations, the implant may be configured to self-expand from the low-profile configuration to the expanded configuration. In other variations, the implant may be expanded (e.g., using a balloon or other device) to move the implant from the low-profile configuration to the expanded configuration. When positioned in the expanded configuration, the legs (103) of the implant may resist movement towards the low-profile configuration, which may allow the legs (103) to support or otherwise press against tissue.

Figure 2C:
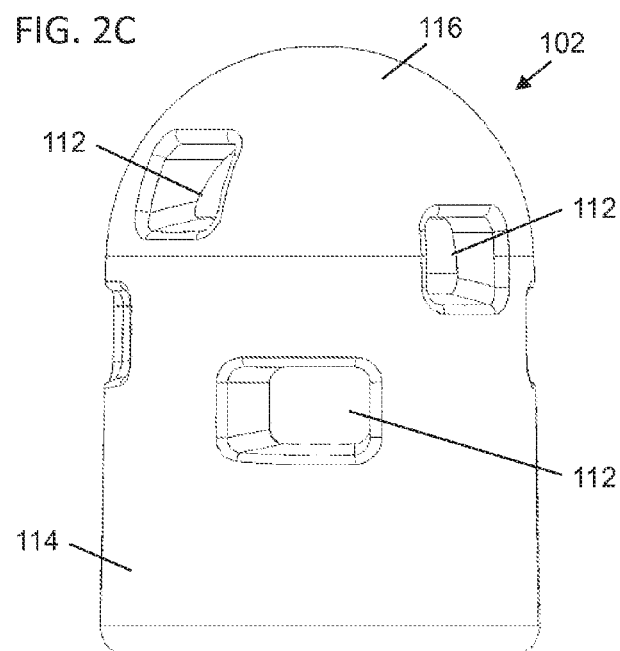

Generally, the hub (102) may act as a junction to join the plurality of legs (103). In some instances the hub (102) may help facilitate advancement of the implant (100) through tissue (e.g., by separating tissue as the hub (102) is advanced therethrough), and/or may be configured to pierce tissue and/or at least partially anchor the implant (100) relative to tissue, as will be discussed in more detail below. FIG. 2C shows a side view of a variation of the hub (102). As shown there the hub (102) may comprise a plurality of apertures (112) extending through the hub (102). The apertures (112) may be configured to connect the legs (103) to the hub (102), as will be discussed in more detail below. As shown there, the hub (102) may comprise a cylindrical portion (114) and a domed portion (116) at a distal end of the hub (102). The domed portion (116) may be configured to engage one or more portions of a crimping device to align the implant (100) with the crimping device, as will be described in more detail below. While shown in FIG. 2C as having both a cylindrical portion (114) and a domed portion (116), it should be appreciated that the hub (102) need not comprise a domed portion (116), or may comprise a tapered portion having a different profile than the domed portion (116). In some variations, the hub (102) may comprise a tapered portion with a pointed distal end, which may be configured to pierce tissue when the pointed distal end is pressed against tissue. In some of these variations, one or more portions of the hub (102) may comprise one or more hooks or barbs, which may help to anchor the hub (102) relative to tissue. In other variations, the hub (102) may not comprise a tapered portion. For example, in some variations cylindrical portion (114) may extend from a proximal end of the hub (102) to a distal end of the hub (102).

Additionally, while the hub (102) is shown in FIGS. 2A-2F as having a circular cross-sectional shape, it should be appreciated that the hub (102) may have any suitable cross-sectional shape (e.g., a circle, oval, rectangle, polygon, triangle, or the like). When the hub (102) comprises a cylindrical portion (114) and a domed portion (116), the cylindrical portion (114) and the domed portion (116) may have the same cross-sectional shape, or may have different cross-sectional shapes. In some variations, one or more portions of the hub (102) may be hollow. For example, in the variation of the hub (102) shown in FIGS. 2A-2F, each of the cylindrical portion (114) and the domed portion (116) may be hollow. When an aperture (112) extends through a hollow portion of the hub (102), the aperture (112) may comprise first and second portions that may be separated by a hollow interior of the hub (102). For example, as shown in a cross-sectional side view in FIG. 2E, an aperture (112) may comprise a first aperture segment (112a) extending through the hub (102) on a first side of the hollow interior (113) of the hub (102) and a second aperture segment (112b) extending through the hub (102) on a second side of the hollow interior (113), such that the first and second aperture segments are separated by the hollow interior (113) of the hub (102). Accordingly, the first aperture segment (112a) and the second aperture segment (112b) may provide an open pathway through the hub (102), which may aid in the assembly of the implant, as discussed in more detail below.

Generally, the plurality of legs (103) of the implant may be formed from a plurality of filaments (104) that are attached to the hub (102). FIG. 2D shows a side view of a variation of a filament (104) suitable for use with the implants (100) described here. As shown there, the filament (104) may comprise a first straight segment (106), a second straight segment (108), and a curved segment (110) positioned between the first straight segment (106) and the second straight segment (108). In some instances the first straight segment (106) may be connected to a first end (117) of the curved segment (110) and the second straight segment (108) may be connected to a second end (119) of the curved segment (110), although it should be appreciated that the filament may comprise one or more additional straight or curved segments positioned between either the first or second straight segments and the curved segment (110). In some instances, the first straight segment (106) may extend from the curved segment (110) at an angle (θ1) relative to a tangent line (120) of the curved segment (110) at the first end (117) of the curved segment (110). Similarly, the second straight segment (108) may extend from the curved segment (110) at an angle (θ2) relative to a tangent line (122) of the curved segment (110) at the second end (119) of the curved segment (110). The angles (θ1) and (θ2) may be the same or may be different, and may be any suitable value (e.g., between about 10 degrees and about 60 degrees, between about 15 degrees and about 45 degrees, less than 10 degrees, or the like). In some instances, one or both of the angles (θ1) and (θ2) may be about 0 degrees, such that the first (106) and/or second (108) straight segments may extend parallel to the tangent lines (120) and (122) respectively.

To attach the filaments (104) to the hub (102), each filament (104) may be advanced through a respective aperture (112) and positioned such that a portion of the filament (104) extends through the hub (102). For example, FIGS. 2E and 2F depict cross-sectional side views of the implant (100) with a filament (104) positioned through an aperture (112) of the hub (102) (only one filament (104) is shown there for the sake of illustration). When the aperture (112) comprises a first aperture segment (112a) and a second aperture segment (112b) separated by a hollow interior (113) of the hub (102) (as shown in FIGS. 2E and 2F), the filament (104) may be positioned such that a portion of the filament (104) extends through each of the first aperture segment (112a), the second aperture segment (112b), and the hollow interior (113).

The filament (104) may be positioned such that any suitable portion of the filament extends through the hub (102). For example, in the variation shown in FIGS. 2E and 2F, the filament (104) may be positioned such that the curved segment (110) is positioned in the aperture (112) and extends through the hub (102). In these variations, positioning the curved segment (110) to extend through the hub (102) may position a first straight segment (106) of the filament (104) on a first side of the hub (102) and the second straight segment (108) on an opposite side of the hub (102). Accordingly, when the filament (104) is positioned as shown in FIGS. 2E and 2F, the filament (104) may define two legs, specifically a first leg (103a) defined by the portion of the filament (104) on a first side of the hub (102) (e.g., a portion of the curved segment (110) and the first straight segment (106)) and a second leg (103b) defined by the portion of the filament (104) on the other side of the hub (102) (e.g., a portion of the curved segment and the second straight segment (108)). Each leg may have a distal end (e.g., where the leg joins the hub (102)) and a proximal end (e.g., at the proximal end of the implant (100)). With the filament (104) positioned through the hub (102), the first (103a) and second (103b) legs may be rotated relative to the hub to move the legs between a low-profile configuration (as shown in FIG. 2E) and an expanded configuration (as shown in 2F). In some variations, as mentioned above, the filament (104) may be biased towards the expanded configuration, which may allow the implant (100) to self-expand when forces holding the implant in a low-profile configuration are removed.

The implant (100) may comprise any number of filaments (104). When the filaments (104) are positioned to extend through a hub (102), the filaments (104) may in turn define twice as many legs (103). For example, in some variations the implant (100) may comprise two filaments (104), which may define four legs (103) when the filaments (104) are positioned to extend through the hub (102). In other variations, the implant (100) may comprise three filaments (104), which may define six legs (103) when the filaments (104) are positioned to extend through the hub (102). In yet other variations, such as the variation shown in FIGS. 2A and 2B, the implant (100) may comprise four filaments (104), which may define eight legs (103) when the filaments (104) are positioned to extend through the hub (102). Additionally, the apertures (112) may be positioned such that the plurality of filaments (104) have different rotational orientations when each filament (104) is positioned in a respective aperture (112). For example, the apertures (112) may be positioned in the hub (102) such that filaments (104) are evenly spaced around the longitudinal axis of the implant. For example, in variations where the filament comprises four filaments (104), the filaments (104) may be positioned such that there is a 45 degree rotation between adjacent filaments (104), such that there is a 45 degree angle between each leg (103) (e.g., when looking at the legs from a top of the implant).

Generally, each leg (103) of the implant (100) may have any suitable length between the proximal and distal end of the leg. In some variations all of the legs (103) may have the same length. This length may be any suitable value, for example, about between about 15 mm and about 30 mm. In some of these variations, each leg (103) may have a length between about 20 mm and about 25 mm. In some of these variations, each leg (103) may have a length of about 20 mm. In others of these variations, each leg (103) may have a length of about 25 mm. In other variations, different legs (103) of the implant may have different lengths between proximal and distal ends of the respective legs. In some of these variations, the implant may comprise a first plurality of legs having a first length between proximal and distal ends of each leg of the first plurality of legs and the a second plurality of legs having a second length between proximal and distal ends of each leg of the second plurality of legs, wherein the second length is longer than the first length. For example, in some variations the first length may be about 20 mm and the second length may be about 25 mm. In some variations where the implant (100) comprises a first plurality of legs having a first length and a second plurality of legs having a second length, the first and second plurality of legs are rotationally oriented such that the legs (103) of the implant alternate between legs of the first plurality of legs and the second plurality of legs (e.g., each leg of the first plurality of legs may be rotationally positioned between two legs of the second plurality of legs). While the number of legs in the first plurality of legs may be equal to the number of legs in the second plurality of legs, it should be appreciated that the first plurality of legs may have more legs than the second plurality of legs, or may have fewer legs than the second plurality of legs.

Generally, the filaments (104) may have any suitable cross-sectional shape. For example, in the variation shown in FIGS. 2A-2F, the filaments (104) may have a rectangular cross-sectional shape. In other variations, the filaments (104) may have an oval cross-sectional shape. In still other variations, the filaments (104) may have a circular cross-sectional shape. The apertures (112) may also have any suitable shape (e.g., a rectangle, oval, circle, or the like). In some variations, the cross-sectional shape of the filament (104) may match the shape of aperture (112) in which the filament (104) is positioned. For example, in the variation shown in FIGS. 2A-2F, the apertures (112) may have a rectangular shape which corresponds to the rectangular cross-sectional shape of the filaments (104). In some variations, it may be desirable to configure the filaments (104) and apertures (112) such that they have non-circular shapes. In these variations, the non-circular nature of the filaments (104) and apertures (112) may reduce or prevent rotation between the filaments (104) and the apertures (112). Additionally, the implant (100) may be configured to fix the plurality of filaments (104) relative to their respective apertures (112). For example, in some variations the filaments (104) may be bonded (e.g., via one or more adhesives or thermal bonding), welded (e.g., via ultrasonic welding), or press-fit to the hub (102).

The implants (100) described above may be formed in any suitable manner. Generally, forming the implant may comprise forming a hub comprising a plurality of apertures extending therethrough, forming a plurality of filaments, and advancing each filament through a respective aperture such that a portion of the filament extends through the hub. The hub and filaments may be formed in any suitable manner (e.g., extrusion, injection-molding, blow-molding, vacuum-formation, casting, or the like), and the hub and filaments may be formed using the same processing techniques or different processing techniques. In some variations, forming the plurality of filaments may comprise extruding the plurality of polymer filaments. In some of these variations, forming the hub may comprise forming the hub using injection molding. In others of these variations, forming the hub may comprise extruding the hub. In others of these variations, the hub may be formed from a laser-cut tube.

Additionally, in some variations, forming the plurality of filaments may include shaping each filament such that the filament comprises one or more straight and/or curved segments, such as discussed above. For example, in some of these variations, some or all of the filaments may be shaped such that the filaments have a first straight portion, a second straight portion, and a curved segment between the first and second straight portions. In some of these variations, advancing each filament through a respective aperture in the hub may include positioning a filament in the aperture such that the curved segment extends through the hub. In some variations, once the filaments have been advanced through the hub, the filaments may be fixed relative to the hub to prevent the filament from sliding relative to the hub. This may be done, for example, by bonding (e.g., thermal bonding, adhesive bonding) or welding (e.g., ultrasonic welding) the filaments to the hub.

Generally, the implant may be formed from any suitable material or combinations of materials. In some variations, the hub and/or the filaments may be formed from one or more materials that are biodegradable, bioerodable, or otherwise erodible. In some variations, the plurality of filaments may be biodegradable, but the hub may not be (or vice versa). In other variations, both the hub and the filaments may be biodegradable. In still other variations, neither the hub nor the filaments may be biodegradable. While in some instances the hub and the plurality of filaments may be formed from the same material or materials, in other variations the hub may be formed from a different material or materials than the material or materials of the plurality of filaments.

In some variations, the hub and/or the plurality of filaments may be formed from one or more polymers. When both the hub and the plurality of filaments are formed from one or more polymers, the hub may be formed from the same polymer (or polymers) as the filaments or may be formed from different polymers than the filaments. The polymers may be biodegradable, but need not be. Examples of biodegradable polymers that may be suitable for use with the implants describe here include, but are not limited to, aliginate, cellulose and ester, dextran, elastin, fibrin, hyaluronic acid, polyacetals, polyarylates (L-tyrosine-derived or free acid), poly($\alpha$-hydroxy-esters), poly($\beta$-hydroxy-esters), polyamides, poly(amino acid), polyalkanotes, polyalkylene alkylates, polyalkylene oxylates, polyalkylene succinates, polyanhydrides, polyanhydride esters, polyaspartimic acid, polybutylene diglycolate, poly(caprolactone), poly(caprolactone)/poly(ethylene glycol) copolymers, poly (carbonate), L-tyrosine-derived polycarbonates, polycyanoacrylates, polydihidropyrans, poly(dioxanone), poly-p-dioxanone, poly(epsilon-caprolactone), poly(epsilon-caprolactone-dimethyltrimethylene carbonate), poly (esteramide), poly(esters), aliphatic polyesters, poly (etherester), poly(ethylene glycol)/poly(orthoester) copolymers, poly(glutarunic acid), poly(glycolic acid), poly (glycolide), poly(glycolide)/poly(ethylene glycol) copolymers, poly(glycolide-trimethylene carbonate), poly(hydroxyalkanoates), poly(hydroxybutyrate), poly(hydroxybutyrate-co-valerate), poly(imino carbonates), polyketals, poly(lactic acid), poly(lactic acid-co-glycolic acid), poly(lactic acid-co-glycolic acid)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)/poly(ethylene glycol) copolymers, poly(lactide)/poly(glycolide) copolymers, polyorthoesters, poly(oxyethylene)/poly(oxypropylene) copolymers, polypeptides, polyphosphazenes, polyphosphoesters, polyphosphoester urethanes, poly(propylene fumarate-co-ethylene glycol), poly(trimethylene carbonate), polytyrosine carbonate, polyurethane, PorLastin or silk-ealastin polymers, spider silk, tephaflex, terpolymer (copolymers of glycolide, lactide or dimethyltrimethylene carbonate), and combinations, mixtures or copolymers thereof. Examples of nonbiodegradable polymers suitable for use with the methods and devices described herein include, but are not limited to poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof. In variations where the implant comprises poly(lactic-co-glycolic acid), the molar percent of lactide or the molar percent of glycolide may be any suitable amount, for example, between about 0% and about 100%, between about 30% and about 100%, between about 50% and about 100%, between about 70% and about 100%, between about 0% and about 70%, between about 30% and about 70%, between about 50% and about 70%, between about 0% and about 50%, between about 30% and about 50%, between about 0% and about 50% and the like. In some variations, the molar ratio of lactide to glycolide is about 10:90, about 85:15, about 15:85, or the like. In variations where the implant comprises a poly(lactic-co-glycolic acid)/poly(ethylene glycol) copolymer, the copolymer may include any suitable amounts of poly(lactic-co-glycolic acid) and poly(ethylene glycol). For example, in some variations the copolymer may comprise about 90% poly(lactic-co-glycolic acid) and about 10% poly(ethylene glycol). It should be further appreciated that the poly(lactic-co-glycolic acid) may have any suitable molar percentages of lactide and glycolide, as described above. Examples of other suitable materials may be found in U.S. patent application Ser. No. 12/779,240, filed on May 13, 2010 and titled "Expandable Devices and Methods Therefor," the content of which is hereby incorporated by reference in its entirety.

In some variations, the implant may be configured to release one or more drugs therefrom. The implant may be configured to release any suitable drugs or agents, such as those described in U.S. patent application Ser. No. 12/779,240, which was previously incorporated by reference. For example, in some variations the implant may be configured to release one or more steroids, such as mometasone furoate. The implant may be configured to release one or more drugs in any suitable manner. In some variations, the implant may comprise one or more drug-releasing coatings, such as those described in U.S. patent application Ser. No. 12/779,240, which was previously incorporated by reference. In other variations, the hub and/or one or more of the filaments may be configured to elute or otherwise release one or more drugs therefrom. The selection of drugs, the timing of delivery, and the overall amount of drug or drugs released may be determined by the intended treatment plan, and may be further fine-tuned to the meet the specific needs of an individual patient.

The implants described here may be delivered using any suitable delivery device, such as, for example, the delivery device (200) shown in FIG. 1. As shown there, the delivery device (200) may comprise a handle (202), an inner shaft (204), and an outer sheath (206). FIGS. 3A and 3B show side views of a distal portion of the delivery device (200). As shown there, the inner shaft (204) may comprise a ball tip (207) and an engagement sleeve (208) covering a portion of the inner shaft (204). The outer sheath (206) may comprise a distal cup (210), which will be described in more detail below.

Generally, the inner shaft (204) may be positioned at least partially within the outer sheath (206), and the inner shaft (204) may be moveable relative to the outer sheath (206). The handle (202) may be configured to move the inner shaft (204) relative to the outer sheath (206). For example, in the variation of the delivery device (100) shown in FIG. 1, the handle (202) may comprise one or more proximal grips (212) and one or more distal grips (214). The proximal grips (212) may be moveable relative to the distal grips (214) to move the inner shaft (204) relative to the outer sheath (206). For example, handle (202) may be configured such that advancement of the proximal grips (212) toward the distal grips (214) advances the inner shaft (204) relative to the outer sheath (206) (as shown in FIG. 3A), and retraction of the proximal grips (212) away from the distal grips (214) retracts the inner shaft (204) relative to the outer sheath (206) (as shown in FIG. 3B).

To load an implant (such as implant (100) depicted in FIG. 1) into the delivery device (200), the inner shaft (204) may be advanced relative to the outer sheath (206) (as shown in FIG. 3A), and a tip of the inner shaft (204) may be positioned in, against, or near the hub (102) of the implant (100). The legs (103) of the implant may be moved to a low-profile configuration (e.g., using a crimping device, as will be described in more detail below) around the inner shaft (204). With the legs (103) of the implant (100) in a low-profile configuration, the outer sheath (206) may be advanced relative to the inner shaft (204) to advance the distal cup (210) over a portion of the legs (103) of the implant. The distal cup (210) may retain the legs (103) in a low-profile configuration until delivery of the implant (100). To deliver the implant (100), the outer sheath (206) may be retracted relative to the inner shaft (204) to retract the distal cup (210), which may in turn expose the legs (103). When exposed, the legs (103) may expand or be expanded to deliver the implant (100). Loading of the delivery device (200) and delivery of the implant (100) will be described in more detail below.

While the inner shaft (204) is shown in FIGS. 3A and 3B as having a ball tip (207) and an engagement sleeve (208), it should be appreciated that in some variations, the delivery device (200) may comprise only one of these features (e.g., either a ball tip (207) or an engagement sleeve (208)) or may not include either of these features. In variations where the delivery device (200) comprises a ball tip (207), the ball tip (207) may facilitate engagement of the delivery device (200) with an implant. Specifically, when the inner shaft (204) is used to push against the hub of implant (e.g., to crimp the implant using one of the crimping devices described here, as will be discussed in more detail below), the rounded nature of the ball tip (207) may cause the ball tip (207) to slide at least partially into a hollow portion of the hub, which may act to center or otherwise locate the ball tip (207) relative to the hub of the implant.

In variations of the delivery devices (200) described here where the inner shaft (204) comprises an engagement sleeve (208), the engagement sleeve (208) may be configured to grip or otherwise increase a frictional force between the inner shaft (204) and one or more legs (103) of the implant (100). Specifically, when the legs (103) of the implant are moved to a low-profile configuration around the inner shaft (204), one or more portions of the legs (103) (e.g., a straight segment of the leg) may contact the engagement sleeve (208). In some variations, the engagement sleeve (208) may comprise a flexible material (e.g., a foam, silicon, or the like), such that contact between the legs (103) and the engagement sleeve (208) may temporarily form a depression in the engagement sleeve (208), which may help to hold the leg (103) relative to the engagement sleeve (208). Additionally or alternatively, the engagement sleeve (208) may be roughened, patterned, or otherwise have a higher coefficient of friction than the inner shaft (204), which may reduce the ability of the legs (103) to slip relative to the engagement sleeve (208) (and thus the delivery device (200). It should be appreciated that the implants described here may be delivered using any suitable implant, such as those described in U.S. patent application Ser. No. 12/779,240, which was previously incorporated by reference.

Also described here are devices for crimping expandable devices. Generally the crimping devices described here may be configured to crimp an implant having a plurality of legs. While the crimping devices are described here as being used to crimp the implant (100) described above with respect to FIGS. 1 and 2A-2F, the crimping devices may be any used to crimp any suitable multi-leg implant, such as those described in U.S. patent application Ser. No. 12/779,240, which was previously incorporated by reference.

Returning to FIG. 1, the crimping device (300) may comprise a housing (302) and a crimping member (304). Generally, the housing (302) may comprise an outer housing (306) and an inner housing (308). The outer housing (306) may be sized and shaped to be held by a user, and the inner housing (308) may be configured to interact with the crimping member (304) to crimp an implant to a low-profile configuration, as will be discussed in more detail below. The inner housing (308) and the outer housing (306) may be formed as a single member, or may be formed separately and joined together. The components of the housing may be formed from any suitable material, such as one or more metals (e.g., stainless steel), plastics (e.g., polyurethane, polycarbonate, polypropylene, or the like), combinations thereof and the like.

Figure 4A:
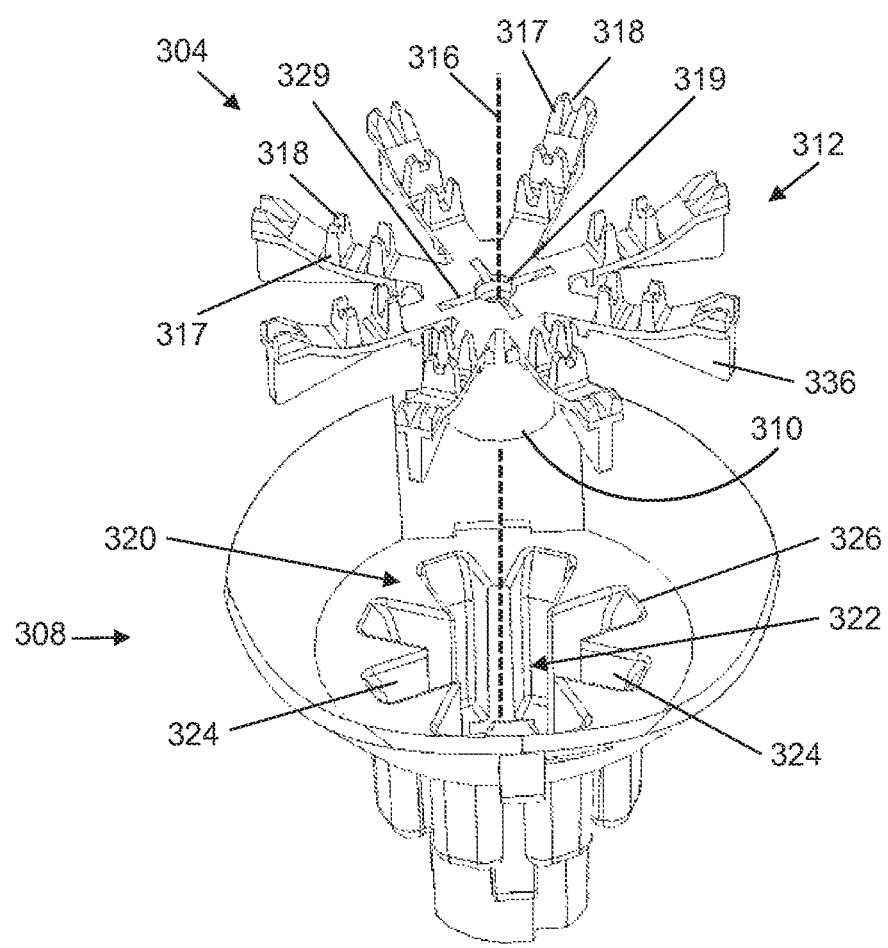
FIG. 4A depicts a perspective view of a portion of a variation of a crimping device described here.
Figure 4B:
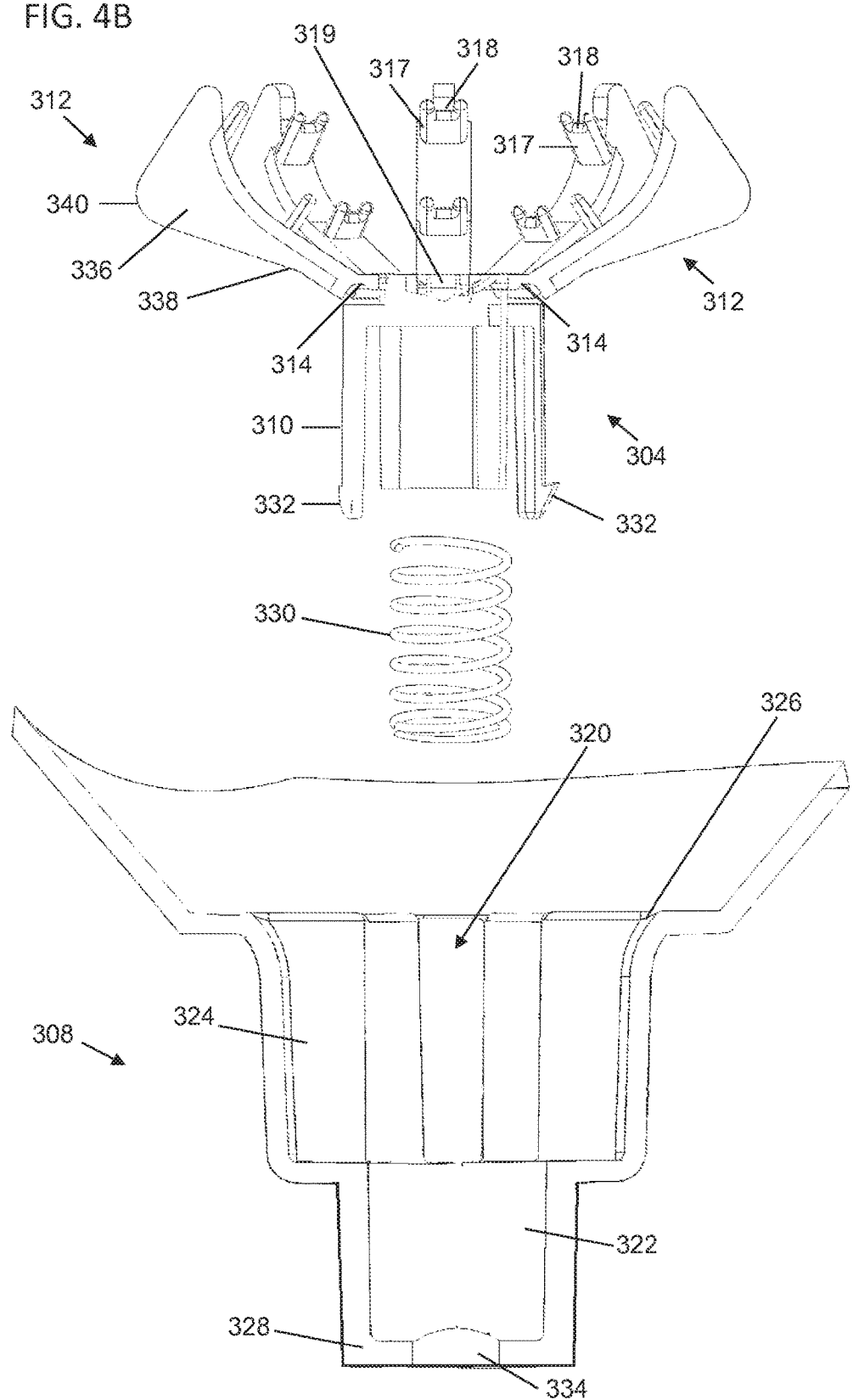
FIG. 4B depicts a cross-sectional side view and FIGS. 4C and 4D depict perspective views of the crimping device of FIG. 4A.

As mentioned above, the crimping member (304) may interact with the inner housing (308) to crimp an implant. To illustrate this, FIGS. 4A and 4B depict exploded perspective and cross-sectional side views, respectively, of the inner housing (308) and the crimping member (304) (the outer housing (306) is not depicted in FIGS. 4A-4F). As shown there, the crimping member (304) may comprise a stem portion (310) and a plurality of arms (312) radially extending from the stem portion (310). Each of the arms (312) may be rotatably connected to the stem portion (310) at a joint (314) such that the arms (312) may be rotated toward or away from a longitudinal axis (316) of the crimping member (304). To rotate the arms (312) relative to the stem portion (310), the crimping member (304) may be withdrawn into a recess (320) of the inner housing (308).

Figure 4C:
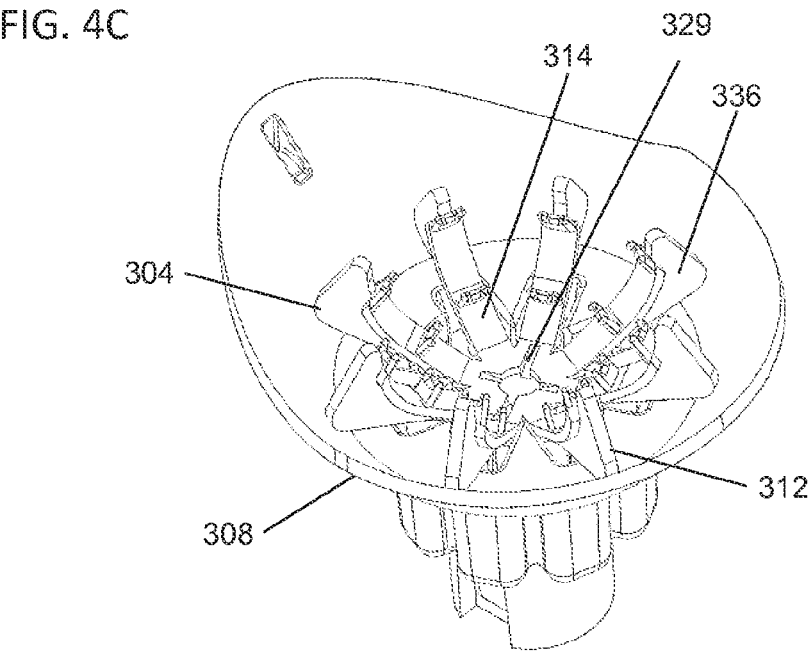
Figure 4D:
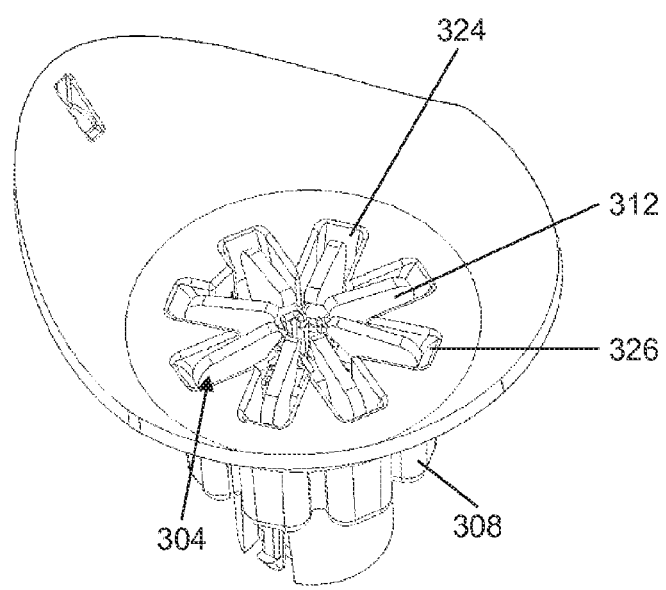

Specifically, the recess (320) may comprise a central recess (322) and a plurality of channels (324) extending radially from the central recess (322). The crimping member (304) may be positioned at least partially in the recess (320) to position the stem portion (310) at least partially within the central recess (322), and may be moved between an open configuration (as shown in FIG. 4C) and a crimping configuration (as shown in FIG. 4D). Generally, the length between a center of the stem portion (310) and a distal end of each arm (312) may be greater than the distance between a center of the central recess (322) to an outer edge (326) of each channel (324). When the crimping member is positioned in the open configuration, each arm (312) may be positioned in a corresponding channel (324) such that the distal end of each arm (312) extends beyond the outer edge (326) of the corresponding channel (324). To move the crimping member (304) to the crimping configuration, the stem portion (310) may be pushed, pulled, or otherwise moved further into the central recess (322) (e.g., toward a bottom surface (328) of the central recess (322)). As the stem portion (310) is moved toward the bottom surface (328), each arm (312) of the crimping member may be pulled into contact with the outer edge (326) of the corresponding channel (324), and the outer edge (326) may act as a fulcrum to rotate each arm (312) relative to the stem portion (310). This may rotate each arm (312) toward a longitudinal axis (316) of the crimping member (304). Additionally, as the arms (312) rotate relative to the stem portion (310), the arms may be drawn at least partially into their respective channels (324) to place the crimping member (304) in the crimping position, as shown in FIG. 4D. During rotation of the arms (312), the arms (312) may engage and move the legs of an implant to crimp the implant to a low-profile configuration, as will be described in more detail below. To return the crimping member (304) to the open configuration (as shown in FIG. 4C), the stem portion (310) may be moved away from the bottom surface (328) of the central recess (322) which may advance the arms (312) at least partially out of the channels (324). As the arms (312) exit the channels (324), they may be configured to rotate away from the longitudinal axis (316) of the crimping member (304).

In some variations, the crimping device (300) may comprise a spring (330) positioned between the stem portion (310) of the crimping member (304) and the bottom surface (328) of the central recess (322). The spring (330) may bias the crimping member (304) towards the open configuration shown in FIG. 4C. As the crimping member (304) is moved into the recess (320) to crimp an implant, the crimping member (304) may push against the spring (330) and may compress the spring (330). When the force or forces that moved the crimping member (304) into the recess (320) are removed, the spring may decompress to return the crimping member (304) to the open configuration.

In some variations, the crimping device (300) may be configured such that the crimping member (304) may not be completely released from the recess (320) of the inner housing (308). For example, in some variations (such as shown in FIG. 4B), the crimping member (304) may comprise one or more latches (332), which may be configured to catch or otherwise engage a portion of the inner housing (308) when the crimping member (304) is moved from the crimping configuration to the open configuration. This engagement between the latch (332) and the inner housing may prevent further movement of the crimping member (304) away from the inner housing (308). In other variations, the crimping member (304) may comprise a pin (not shown)

that extends through an opening (334) in the bottom surface (328) of the central recess (322). The pin may be slidable relative to the bottom surface (328), and may comprise a stop (e.g., a portion of the pin or a member attached thereto having a diameter greater than that of the opening (334)) that is positioned beneath an opposite side of the bottom surface (328) as the rest of the crimping member (304). When the crimping member (304) is moved from the crimping configuration to the open configuration, the stop may be prevented from passing through the opening (334), and may prevent further movement of the crimping member (304) away from the recess (320).

The arms (312) may be configured to rotate relative to stem portion (310) in any suitable manner. In some variations, the joint (314) may comprise a pin joint that connects the arm (312) to the stem portion (310). In other variations, the arm (312) may be configured to rotate via deformation of a portion of the arm. For example, in some variations, such as that shown in FIGS. 4A-4F, the joint (314) may comprise a living hinge. In these variations, the material of the living hinge that connects an arm (312) to the stem portion (310) may be biased away from the longitudinal axis (316) of the crimping member (304), such that when the crimping member (304) is moved from the crimping configuration to the open configuration, the arm (302) may be configured to rotate away from the longitudinal axis (316) of the crimping member (304). Additionally or alternatively, the arms (312) may comprise one or more spring members (not shown) configured to rotate the arms (312) away from the longitudinal axis (316) of the crimping member (314) as the crimping member (304) is moved from the crimping configuration to the open configuration.

Each leg of an implant may be engaged by a respective arm (312) of the crimping member (304), such that rotation of the arms (312) toward the longitudinal axis (316) of the crimping member (304) also may rotate the legs of the implant relative to a low-profile configuration. To engage a leg of an implant, an arm (312) of the crimping member (304) may comprise one or more holders (317). Generally, a holder (317) may extend from a corresponding arm (312) and may comprise a channel (318) sized and configured to receive a portion of the leg of the implant. When the implant is initially positioned relative to the crimping member (304), each leg may be positioned in the channels (318) of the one or more holders (317) of a corresponding arm (312). When positioned in the channels (318) of one or more holders (317), each leg may be moved with a corresponding arm (312) as that arm (312) rotates relative to the stem portion (310). Each arm (312) of the crimping member (304) may comprise any suitable number of holders (e.g., one, two, three, or four or more holders). For example, the arms (312) are shown in FIG. 4A as each having three holders (317) and are shown in FIGS. 4B-4F as each having two holders (317). In other variations, the arms (312) may not comprise any holders (317). In some of these variations, the arm may comprise a channel extending along a portion of length of the arm (312), and the channel may be sized and configured to receive a portion of the leg of an implant, which may allow the arm itself to act as a holder as previously discussed.

In some variations, the height of one or more arms (312) of the crimping member (304) may vary along the length of the arm. For example, in the variation of the crimping device shown in FIGS. 4A-4F, the arms (312) may each comprise a wing portion (336), in which the height of the wing increases along the wing portion from a proximal end (338) of the wing portion (336) to a distal end (340) of the wing portion (336). When the arms (312) are pulled into the channels (324) of the recess (320) of the inner housing (308), the increasing height of the wing portion (336) may bring an upper surface of each arm (312) closer to the longitudinal axis (316) of the stem portion (310). When the arms (312) include one or more holders (317) or are otherwise configured to engage the legs of an implant, the increasing height of the wing portions (336) may allow the arms (312) to bring the legs closer to a longitudinal axis of the implant, thereby increasing the degree of crimping of the implant.

In some variations, the stem portion (310) may also comprise one or more structures configured to engage a portion of the implant. For example, in the variation of the crimping device (300) shown in FIGS. 4E-4F, the stem portion (310) may comprise an indentation (319) sized to receive a portion of the hub of an implant. In these variations, a hub of an implant may be positioned such that at least a portion of the hub rests within the indentation (319) of the stem portion (310). This may allow for repeatable positioning of the implant relative to the crimping member (304), and may also reduce or prevent shifting or slipping of the implant relative to the crimping member (304) during crimping. For example, in some variations, the indentation (319) may comprise a hemispherical portion. When the hub of an implant comprises a domed portion (such as described in more detail above), the domed portion of the hub may be centered in the hemispherical portion of the indentation (319), which may help to align the implant relative to the crimping member (304). Additionally, in some variations (such as shown in FIGS. 4A and 4C) the stem portion (310) may additionally comprise one or more slots (329) extending radially from the indentation (319). Each slot (329) may be aligned with an arm (312) of the crimping member (304), and may be sized to receive a portion of a leg of an implant when a hub of the implant is position in the indentation (329). Accordingly, a slot (329) may act as a keyway slot which may prevent or limit rotation of the implant relative to the crimping member (304) when a leg is at least partially positioned in the slot (329). While shown in FIGS. 4A and 4C as having four slots (329), the stem portion (310) of the crimping member (304) may have any suitable number of slots (e.g., one, two, three, four, or five or more slots). In some variations, the stem portion (310) may comprise at least as many slots (329) as the crimping member (304) has arms (312). In these variations, a slot (329) may be aligned with each arm (312) of the crimping member. In some variations where the stem portion (310) comprises an indentation and/or one or more slots configured to receive one or more portions of an implant, the indentation and/or slots may be sized and configured to form a press fit with the implant to temporarily hold the implant relative to the stem portion (310). In these variations, the implant may be pulled away from the stem portion (310) (e.g., using a delivery device) to disengage the implant from the stem portion (310).

FIGS. 4E and 4F depict a manner in which the crimping member (304) may be used to crimp the implant (100) (described above with respect to FIGS. 1 and 2A-2F) to a low-profile configuration. It should be appreciated, however, that the crimping device may be used to crimp any suitable device, such as discussed above. As shown in FIG. 4E, the implant (100) may be positioned such that each leg (103) of the implant (100) is engaged by a corresponding arm (312) of the crimping member (304). In variations where the arms (312) comprise one or more holders (317), one or more of the legs (103) may positioned within channels (318) of one or more holders (317) of the corresponding arms (312) (it should be appreciated that the number of holders (317) of a given arm (312) that engage a leg (103) may increase during the crimping). Additionally, the hub (102) of the implant may be positioned to engage the stem portion (310) of the crimping member (312). For example, as shown in FIG. 4E, at least a portion of the hub (102) may be positioned within an indentation (319) in the stem portion (310). In some instances, this may act to align the implant (100) relative to the crimping member (304). In some variations, one or more of the legs (102) may be positioned corresponding slots (329) of the stem portion (310), which may further align the implant (100) relative to the crimping member (304). In some variations, the indentation (319) and/or slots (329) may temporarily hold the implant (100) in place relative to the stem portion (310).

With each leg (103) of the implant engaged by a corresponding arm (312) of the crimping member (304), the crimping member may be moved into the recess (320) of the inner housing (308) (which is not shown in FIGS. 4E and 4F) to move the crimping member (304) from an open configuration to a crimping configuration. As discussed above, this may cause the arms (312) to rotate toward the longitudinal axis of the stem portion (310) at the joints (314), and the engagement between the legs (102) and the respective arms (312) of the crimping member (304) may cause the arms (312) to rotate the legs (102) toward a low-profile configuration, as illustrated in FIG. 4F. The crimped implant (100) may also be coupled to a delivery device and delivered to the body, as will be described in more detail below.

In some variations, a delivery device may assist in the operation of the crimping device. For example, FIGS. 4E and 4F depict how the delivery device (200) described above with respect to FIGS. 1, 3A, and 3B may be used with the crimping device (300) to crimp the implant (100). It should be appreciated that the crimping device (300) may be used in conjunction with any suitable delivery device, or may be operated independently of a delivery device. When the crimping member (304) is placed in an open configuration and the implant (100) is positioned such that each leg (103) of the implant is engaged by a respective arm (312) of the crimping member (304), as discussed above with respect to FIG. 4E, the delivery device (200) may be configured to engage a portion of the implant (100). Specifically, a distal tip of the inner shaft (204) (e.g., the ball tip (207)) may be placed into contact with the hub (102) of the implant (100) to press the hub (102) against the stem portion (310) of the crimping member (304), as shown in FIG. 4E. When the hub (102) is at least partially hollow, at least a portion of the tip of the inner shaft (204) may extend at least partially into the hollow interior of the hub (102). When a portion of the hub (102) is positioned within an indentation (319) of the stem portion (310), the force applied by the inner shaft (204) to the hub (102) may help to hold the hub (102) relative to the indentation (319). This may reduce the likelihood that the implant (100) will shift relative to the crimping member (304) during crimping.

With the inner shaft (204) pressed against the hub (102), the delivery device (200) may be advanced to push the crimping member (304) into the recess (320) of the inner housing (308). In some variations, the outer sheath (206) and distal cup (210) may be retracted relative to the inner shaft (204) prior to or during the movement of the crimping member (304) into the recess (320). As the crimping member (304) is pushed into the recess (320), the crimping member (304) may move from an open configuration to the crimping configuration, which may rotate the legs (103) relative to the hub (102) into a low-profile configuration, as discussed above. Rotation of the legs (103) to the low-profile configuration may position the legs (103) into contact with or substantially parallel to the inner shaft (204) of the delivery device, such as shown in FIG. 4F. In some variations, the legs (103) of the implant (100) may contact or otherwise engage an engagement sleeve (208) of the inner shaft (204). With the arms (312) of the crimping member (304) holding the legs in a low-profile configuration, the outer sleeve (206) of the delivery device (200) may be advanced relative to the inner shaft (204) to advance the distal cup (210) to cover at least a portion of the legs (103). This may act to hold the legs (103) of the implant (100) between the distal cup (210) and the inner shaft (204) of the delivery device (200), and thus may couple the implant (100) thereto.

With the delivery device (200) coupled to the implant (100), the delivery device (200) may then be withdrawn relative to the crimping member (304). This may cause the crimping member (304) to return to the open configuration (e.g., due to the biasing force provided by a spring (330) as discussed above), which release the engagement between the crimping member (304) and the implant (100). The delivery device (200) may then be used to deliver the implant to a target location within a patient's body. To deliver the implant (100), the distal cup (210) may be withdrawn (e.g., by retracting the outer sheath (206) relative to the inner shaft (204)) to expose the legs (103) of the implant (100). The implant (100) may then be expanded (either by self-expansion or via a device such as a balloon) in the patient to press against, dilate, or otherwise hold tissue in the patient.

Figure 5A:
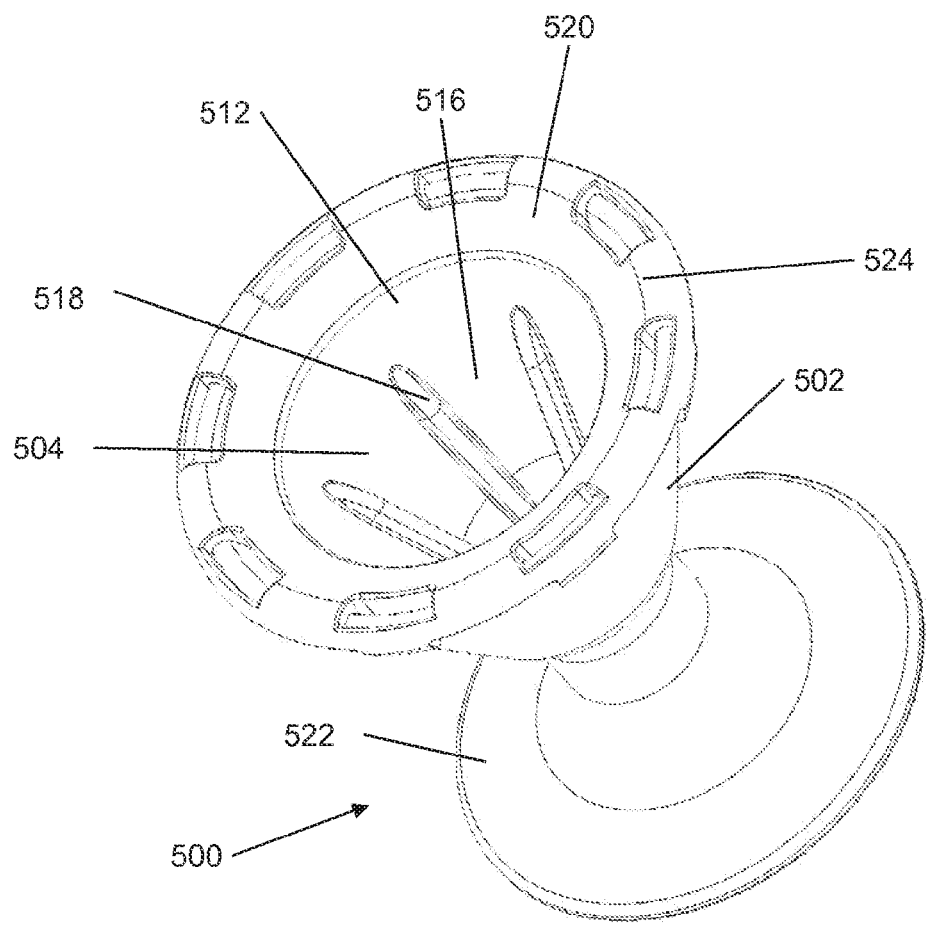
FIGS. 5A-5D depict perspective, top, side, and cut-away side views, respectively, of the a crimping device described here.
Figure 5B:
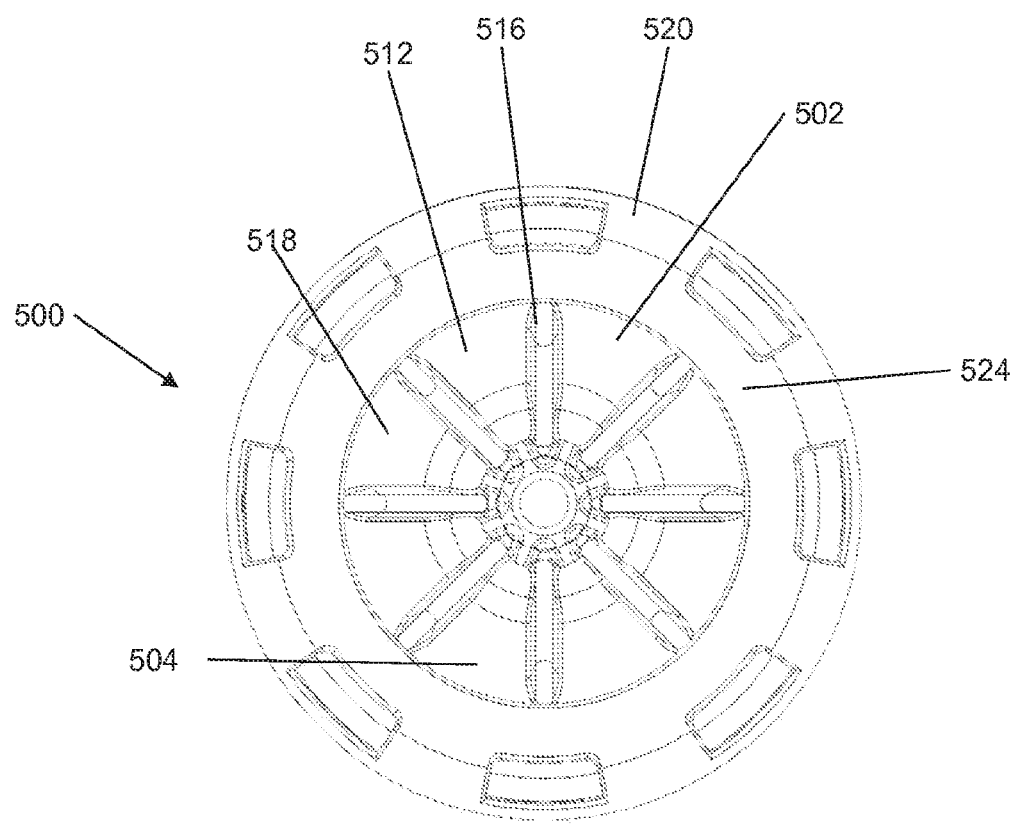
Figure 5C:
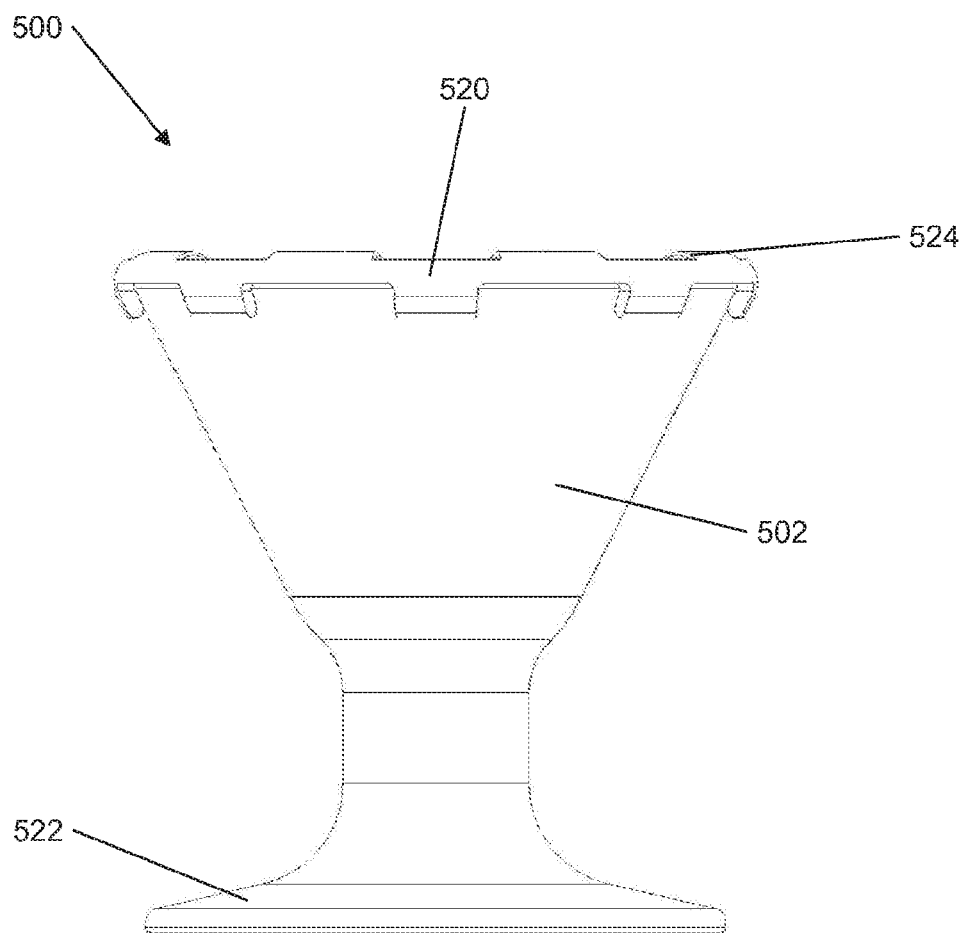
Figure 5D:
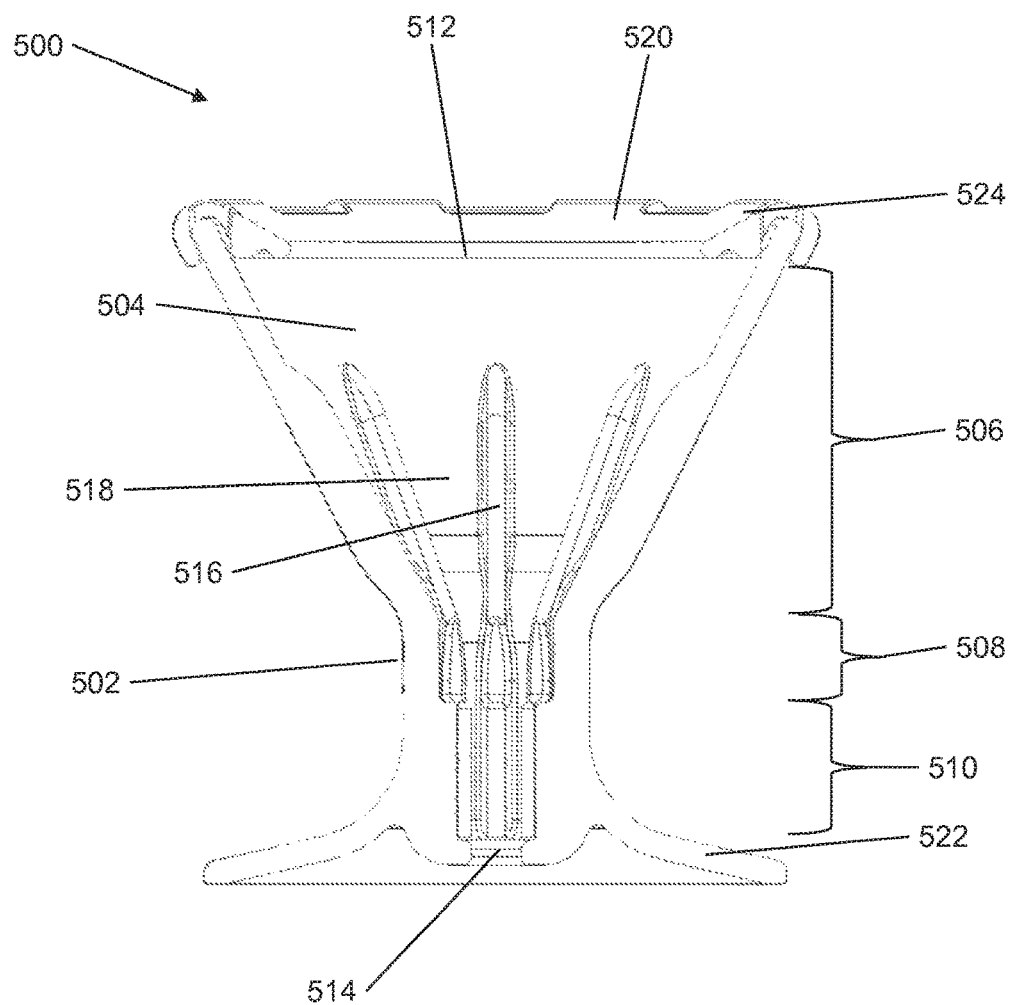

FIGS. 5A-5D depict another variation of a crimping device (500) described here. Specifically, FIGS. 5A-5D show perspective, top, side, and cross-sectional side views, respectively, of the crimping device (500). As shown there, the crimping device may comprise a housing (502) defining a crimping chamber (504) extending at least partially into the housing (502) from a proximal opening (512) in the housing (502). As shown in FIG. 5D, the crimping chamber (504) may comprise a first segment (506), a second segment (508), and a third segment (510) The first segment (506) of the crimping chamber (504) may extend between a proximal opening (512) in the housing (502) to a proximal end of the second segment (508). The second segment (508) may, in turn, extend from a distal end of the first segment (506) to a proximal end of the third segment (510), while the third segment (510) may extend from a distal end of the second segment (508) to a distal end (514) of the crimping chamber (504). In some variations, the housing (502) may comprise a distal opening at a distal end (514) of the crimping chamber (504).

The housing (502) may comprise a plurality of ribs (516) positioned in the crimping chamber (504). The plurality of ribs (516) may define a plurality of channels (518) in the crimping chamber (504), with each channel (518) defined between adjacent ribs (516). The ribs (516) may extend through some or all of the segments of the crimping chamber (504). For example, in the variation shown in FIGS. 5A-5D, the plurality of ribs (516) and plurality of channels (518) may extend through each of the first segment (506), second segment (508), and third segment (510). In some of these variations, the plurality of ribs (516) and plurality of channels (518) may extend from a proximal end of the crimping chamber to a distal end of the chamber. In others of these variations, the plurality of ribs (516) and the plurality of channels (518) may extend only partially through the first segment and/or third segment (510). For example, in the variation shown in FIGS. 5A-5D, the plurality of ribs (516) and plurality of channels (518) may extend from the distal end of the third segment (510), along the second segment (508), and partially along the first segment (506) (e.g., the ribs (516) may terminate distally of the proximal opening (512) of the housing (502)). Additionally or alternatively, the ribs (516) and channels (518) may extend along only a portion of the third (510) segments.

In some variations, one or more of the first segment (506), second segment (508), and third segment (510) may not have any ribs (516) positioned in that segment. For example, in some variations the first segment (506) may not include any ribs (516). In some of these variations, the housing (502) may comprise a plurality of ribs (516) which may extend at least partially through the second segment (508) and at least partially through the third segment (510). In other variations, the second segment (508) may not include any ribs (516). In some of these variations, the first segment (506) may comprise a first plurality of ribs (516) and the third segment (510) may comprise a second plurality of ribs. In some variations, the first plurality of ribs (516) may have the same number of ribs (516) as the second plurality of ribs (516), and in some of these variations, each rib of the first plurality of ribs (516) may be aligned with a corresponding rib of the second plurality of ribs (516).

It should be appreciated that in some instances, different ribs (516) of the plurality of ribs (516) may extend through different segments or combinations of segments, such that different segments of the crimping chamber (504) may have differing numbers of ribs (and thus differing number of channels) positioned therein. For example, in some variations, the plurality of ribs (516) positioned in the crimping chamber (504) may comprise a first plurality of ribs (516) which may extend at least partially along each of the first segment, second segment, and third segment, and a second plurality of ribs (516) which may extend at least partially along the first segment. In these variations, the first segment (506) may include a first number of ribs and the second segment (508) and third segment (510) may include a second number of ribs less than the first number of ribs.

Generally, each segment of the crimping chamber (504) may have an inner diameter and an outer diameter. Generally the outer diameter may represent the outermost profile of the crimping chamber (504), while the inner diameter may represent a profile of the crimping chamber (504) that represents unobstructed space within the crimping chamber (504). The wall of the housing (502) may define the outer diameter of the crimping chamber (504). In portions of the crimping chamber (504) that do not include ribs (516), the inner diameter may be equal to the outer the diameter. In portions of the crimping chamber that do include a plurality of ribs (516) extending inwardly from wall of the housing (502), the tips of the ribs (516) may define the inner diameter of the crimping chamber (504). In these variations, the channels (518) defined between adjacent ribs (516) may extend from the inner diameter to the outer diameter. Accordingly, the depth of each channel (518) may be defined by the height of the adjacent ribs (516).

Each segment of the crimping chamber (504) may have any suitable inner and outer diameters. For example, when the crimping chamber (504) is used to crimp an implant having a plurality of legs moveable between a low-profile and an expanded configuration (such as implant 100 described above), the first segment (506) may be configured to house the implant in its expanded (e.g., uncrimped) configuration. In these variations, at least a portion of the first segment (506) may have an outer diameter greater than or equal to the largest diameter of implant. For example, in variations where the crimping device (500) is configured to crimp a variation of the implant (100) described above with respect to FIGS. 2A-2D, at least a portion of the first segment (506) may have an outer diameter greater than or equal to a diameter defined by the proximal ends of the legs (103).

In some variations, such as that shown in FIGS. 5A-5D, the outer diameter of first segment (506) may be tapered between a first diameter at a proximal end of the first segment (506) and a second diameter at a distal end of the first segment (506). For example, in some variations, the outer diameter of the first segment (506) may taper between about 30 mm at a proximal end of the first segment (506) and about 8 mm at a distal end of the first segment (506). As used here, "about" means±5%. In other variations, the outer diameter of the first segment (506) may taper between about 25 mm at a proximal end of the first segment (506) and about 8 mm at a distal end of the first segment (506). In some of these variations, the inner diameter of the first segment (506) may taper between a proximal end of the first segment (506) to the distal end of the first segment (506). The tapering outer diameter of the first segment (506) may assist in crimping of the implant, such as described in more detail below. It should be appreciated that while the entire first segment (506) is shown in FIGS. 5A-5D as having a tapered outer diameter, it should be appreciated that in some instances one or more portions of the first segment (506) may have a uniform outer diameter. For example, in some variations, the first segment (506) may comprise a distal portion having an outer diameter that tapers between a first diameter and a second diameter smaller than the first diameter, and a proximal portion having a uniform outer diameter which may be greater than or equal to the first diameter.

In variations in which the first segment (506) comprises a plurality of ribs (516) and channels (518) extending at least partially along the first segment (506), the legs of the implant may be at least partially positioned within the plurality of channels (518) when the implant is positioned in the first segment (506), which may align the implant relative to the crimping chamber (504). In some variations, each leg may be positioned in a separate channel (518). In these variations, first segment (506) of the crimping chamber (504) may have at least as many channels (518) as legs of the implant. In other variations, multiple legs (e.g., two, three, or more legs) may be positioned in individual channels (518) of the first segment (506). In these variations, the first segment (506) may have fewer channels (518) than the number of legs of the implant. While the first segment (506) is shown in FIGS. 5A-5D as having eight ribs (516) defining eight channels (518), it should be appreciated that the first segment (506) may include any suitable number of ribs and channels (e.g., two, three, four, five, six, or seven or more ribs and channels).

In some variations, the housing (502) may comprise a lip (520) located at the proximal end of the crimping chamber (504). The lip (520) may extend inward from the housing (502) to define an opening smaller than may be smaller than the outer diameter of the proximal end of the first segment (506). The opening of the lip (520) may define the proximal opening (512) of the crimping chamber (504). Accordingly, the diameter of the proximal opening (512) may be smaller than the outer diameter of the proximal end of the first segment (506). In some of these variations, having a proximal opening (512) with a diameter smaller than the outer diameter of the proximal end of the first segment (506) may help to temporarily hold the implant within the crimping chamber (504). For example, the diameter of the opening of the lip (520) may be smaller than the largest diameter of an implant in when in an expanded configuration (e.g., the diameter defined by the proximal ends of the legs (103) of implant (100) in the expanded configuration). Accordingly, when the implant is placed in the first segment (506) in an expanded configuration, the implant may be temporarily prevented from exiting the crimping chamber (504) through the proximal opening (512). To remove the implant from the crimping chamber (504), the implant may be moved from an expanded configuration to a low-profile configuration, as discussed in more detail below.

In some instances, the lip (520) may be formed integrally with the housing (502). In other variations, such as shown in FIGS. 5A-5D, the lip (520) may be formed as part of a cap (524) that may be connected to the housing (502). In some instances, the cap (524) may be removably connected to from the housing (502). In these variations, the cap (524) may be disconnected from the housing (502) to remove the lip (520) from the housing (502). This in turn, may increase the size of the proximal opening (512) of crimping chamber (504), which may facilitate placement of an implant (e.g., implant (100)) into the crimping chamber (504). The cap (524) may then be connected to the housing (502) (e.g., which may reduce the size of the proximal opening (512)). which may hold the implant (e.g., implant (100)) in the crimping chamber (504) as discussed immediately above. In instances where the lip (520) is integrally formed as part of the housing (502) or a cap (524) comprising the lip (520) is fixedly attached to the housing (502), an implant (e.g., implant (100)) may be inserted into the first segment (506) of the crimping chamber (504) past the lip (520) by temporarily moving the implant toward the low-profile (e.g., crimped) configuration (e.g., by flexing the legs (103) of implant (100) toward a low-profile configuration), to temporarily reduce the outer profile of the implant, and inserting the implant into the proximal opening (512) of the crimping chamber (504). In some of these instances, the implant may return toward the expanded configuration after being inserted past the lip (520) into the first segment (506).

When an implant is positioned in the first segment (506) of the crimping chamber (504), the implant may be moved from the first segment (506) to the second segment (508) to crimp or partially crimp the implant. Generally, the second segment (508) may have an outer diameter that corresponds to a desired outer profile of the implant. For example, in variations where it may be desirable to reduce the implant to a diameter of about 8 mm, the outer diameter of the second segment (508) may be about 8 mm. It should also be appreciated that in some variations where the outer diameter of the first segment (506) tapers from a first diameter at a proximal end of the first segment (506) and a second diameter at a distal end of the first segment (506), the second diameter of the first segment (506) may be equal to the outer diameter of the second segment (508). For example, in variations where the outer diameter of the first segment (506) is tapered from a first diameter at a proximal end of the first segment (506) to about 8 mm at the distal end of the first segment (506), the second segment (508) may have an outer diameter of about 8 mm.

As a portion of implant is moved into the second segment (508) of the crimping chamber, the outer diameter of that portion of the implant may be crimped to the outer diameter of the second segment (508) to allow that portion of the implant to fit within the second segment (508), as will be discussed in more detail below. As mentioned above, in some variations, the second segment (508) may not have any ribs (516) positioned therein. In variations that do include a plurality of ribs (516) defining a plurality of channels (518), the legs of the implants may be at least partially housed in the plurality of channels (518) as the implant is advanced into the second segment (508). As discussed above with respect to the first segment (506), in some variations, each leg may be positioned in a separate channel (518) of the second segment (508). In these variations, second segment (508) of the crimping chamber (504) may have at least as many channels (518) as legs of the implant. In other variations, multiple legs (e.g., two, three, or more legs) may be positioned in individual channels (518) of the second segment (508). In these variations, the second segment (508) may have fewer channels (518) than the number of legs of the implant. While the second segment (508) is shown in FIGS. 5A-5D as having eight ribs (516) defining eight channels (518), it should be appreciated that the second segment (508) may include any suitable number of ribs and channels (e.g., two, three, four, five, six, or seven or more ribs and channels), which may or may not be the same number of ribs and channels as the first segment (in variations where the first segment comprises a plurality of ribs and a plurality of channels). In instances where a plurality of ribs (516) and plurality of channels (518) extend from the first segment (506) into the second segment (508), the ribs (516) and channels (518) may help maintain alignment of the implant relative to the crimping chamber (504) as the implant is moved from the first segment (506) to the second segment (508), as will be discussed in more detail below.

Additionally, in some variations, the second segment (508) of the crimping chamber may be sized to receive an outer sheath of a delivery device (e.g., the outer sheath (206) of the delivery device (200) described above with respect to FIGS. 3A and 3B above) therein. In these variations, the inner diameter of the second segment (508) may be greater than or equal to the outer diameter of a distal portion of the outer sheath of the delivery device. For example, in variations where the outer sheath of a delivery device has a diameter of about 6 mm, the inner diameter of the second segment (508) may be at least about 6 mm (e.g., about 6 mm). In some variations, the second segment (508) may have an inner diameter of about 6 mm and an outer diameter of about 8 mm. The outer sheath may be inserted into the second segment (508) during crimping to hold the implant in a low profile configuration, as will be discussed in more detail below. It should be appreciated that while the second segment (508) is shown in FIGS. 5A and 5B as having uniform inner and outer diameters, in some instances the inner diameter, the outer diameter, or both the inner and outer diameters may be tapered along a length of the second segment.

The third segment (510) may be configured to receive a portion of the implant as the implant is moved from the second segment (508). In some variations, such as shown in FIGS. 5A-5D, the outer diameter of the third segment (510) may be equal to the outer diameter of the second segment (508) (e.g., in some variations where the second segment (508) has an outer diameter of about 8 mm, the third segment (510) may have an outer diameter of about 8 mm). In other variations, the outer diameter of the third segment (510) may be smaller than the outer diameter of the second segment (508). In these variations, the implant may be further crimped as a portion of the implant moves from the second segment (508) to the third segment (510) (e.g., the outer diameter of that portion of the device may be crimped to the outer diameter of the third segment (510) which may allow that portion of the implant to fit within the third segment (510)).

In variations where the second segment (508) is sized to receive an outer sheath of a delivery device (e.g., where the second segment (508) has an inner diameter greater than an outer diameter of the outer sheath), the third segment (510) may be sized to prevent the outer sheath from being advanced from the second segment (508) into the third segment (510). In some of these variations, the inner diameter of the third segment (510) may be smaller than an outer diameter of the outer sheath of the delivery device. For example, in instances where the outer sheath of the delivery device has an outer diameter or about 6 mm, the inner diameter of the third segment (510) may be less than about 6 mm (e.g., about 3.5 mm, between about 3.5 mm and about 4 mm). In variations where the third segment (510) comprises a plurality of ribs (516), the plurality of ribs (516) may define the inner diameter such that the outer sheath of the delivery device catches on or otherwise engages the ribs (516) of the third segment (510) during advancement of the outer sheath, which may prevent the outer sheath from being advanced into the third segment (510), as discussed in more detail below.

In variations where the crimping device (500) is used to crimp an implant having a hub and a plurality of legs extending from the hub, the third segment (510) may be configured to accommodate the hub of the implant. For example, the inner diameter of the third segment (510) may be greater than or equal to the outer diameter of the hub. In variations where the hub of the implant has an outer diameter of about 3.5 mm, the inner diameter of the third segment (510) may be at least about 3.5 mm (e.g., about 3.5 mm). In some instances, it may be desirable to size the inner diameter of the third segment (510) to be equal to or slightly larger (e.g., less than 1 mm larger) than the outer diameter, which may help to center the hub within the inner diameter of the third segment (510) during advancement of the implant. In some variations, the inner diameter of the third segment (510) may greater than or equal to an outer diameter of a hub of the implant and may be less than the outer diameter of an outer sheath of a delivery device.

In some variations, the height of the third segment (510) may be sized such only a portion of the implant may be received in the third segment (510). For example, in these variations the height of the third segment (510) may be less than the height of the implant when the implant is crimped. Accordingly, when the implant is advanced into the third segment (510) at least a portion of the implant (e.g., a proximal portion of the legs of the implant) may extend out of the third segment (510) (e.g., into the second segment (508)). In variations where the inner diameter of the third segment (510) is smaller than the outer diameter of an outer sheath (e.g., which may prevent the outer sheath from entering the third segment (510)), the height of the third segment (510) may facilitate placement of the outer sheath of the delivery device at a predetermined position along the implant.

As mentioned above, in some variations the third segment (510) may include a plurality of ribs (516) positioned therein and defining a plurality of channels (518). In these variations, the legs of the implants may be at least partially housed in the plurality of channels (518) as the implant is advanced into the third segment (510). As discussed above with respect to the second segment (508), in some variations, each leg may be positioned in a separate channel (518) of the third segment (510). In these variations, third segment (510) of the crimping chamber (504) may have at least as many channels (518) as legs of the implant. In other variations, multiple legs (e.g., two, three, or more legs) may be positioned in individual channels (518) of the third segment (510). In these variations, the third segment (508) may have fewer channels (518) than the number of legs of the implant. While the third segment (510) is shown in FIGS. 5A-5D as having eight ribs (516) defining eight channels (518), it should be appreciated that the third segment (510) may include any suitable number of ribs and channels (e.g., two, three, four, five, six, or seven or more ribs and channels).

In variations where the second segment comprises a plurality of ribs (516) positioned therein, some or all of the ribs (516) of the second segment (508) may extend from the second segment (508) into the third segment (510), the ribs (516) and channels (518) may help maintain alignment of the implant relative to the crimping chamber (504) as the implant is advanced into the third segment (510). In some of these variations, the number of ribs and channels in the third segment (510) may be equal to the number of ribs and channels in the second segment (508), although it should be appreciated that in some instances the third segment (510) may have more or fewer ribs and channels than the second segment (508). As mentioned above, the inner diameter of the second segment (508) may be larger than the inner diameter of the third segment (510), while the outer diameter of the second segment (508) may be the same as the outer diameter of the third segment (510). In some of these variations, each of the second and third segments may comprise a plurality of ribs defining a plurality of channels, and the channels (518) may in the second segment (508) may be shallower than the channels (518) in the third segment (510).

In some variations, such as the variation shown in FIGS. 5A-5D, the housing may further comprise a base (522). The base may be integrally formed with the housing (502), as shown in FIGS. 5A and 5C-5D, or it may be attached to the housing (502). The base (522) may be located at the distal end of the housing (502), near the distal end of the third segment (510) of the crimping chamber (504). In some variations, the base (522) may have a larger diameter than the housing (502) surrounding the third segment (508), and may provide a surface on which the crimping device (500) may be rested. Additionally or alternatively, the base (522) may provide stability during crimping when a delivery device and implant are pressed distally into the crimping chamber (504), as described in more detail below.

Figure 6A:
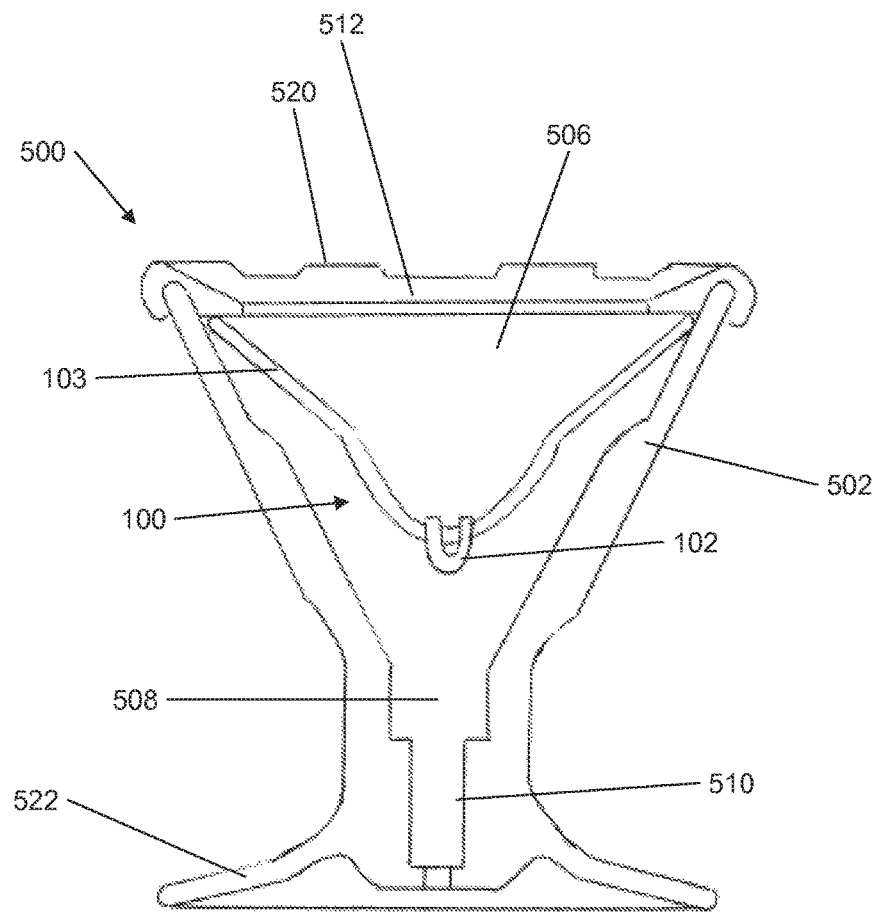
FIGS. 6A-6C depict cross-sectional side views of the crimping device of FIGS. 5A-5D in operation.
Figure 6B:
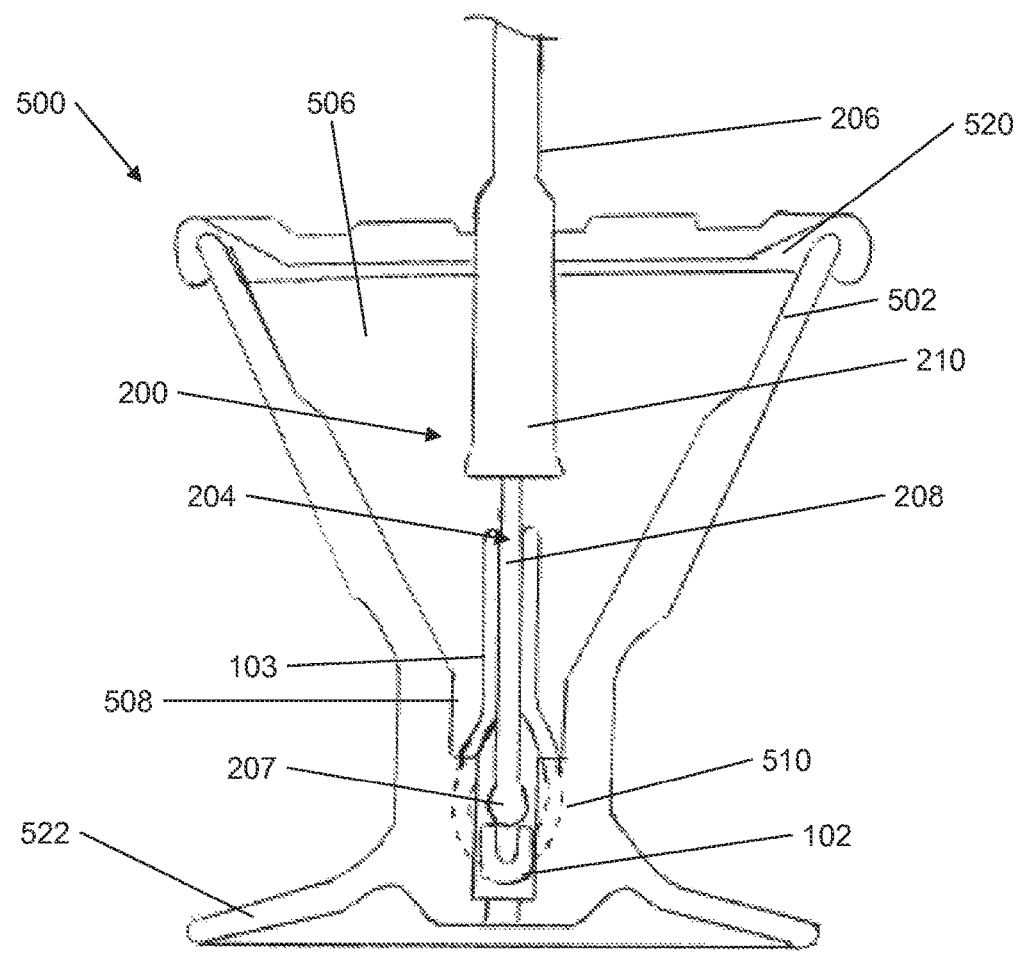
Figure 6C:
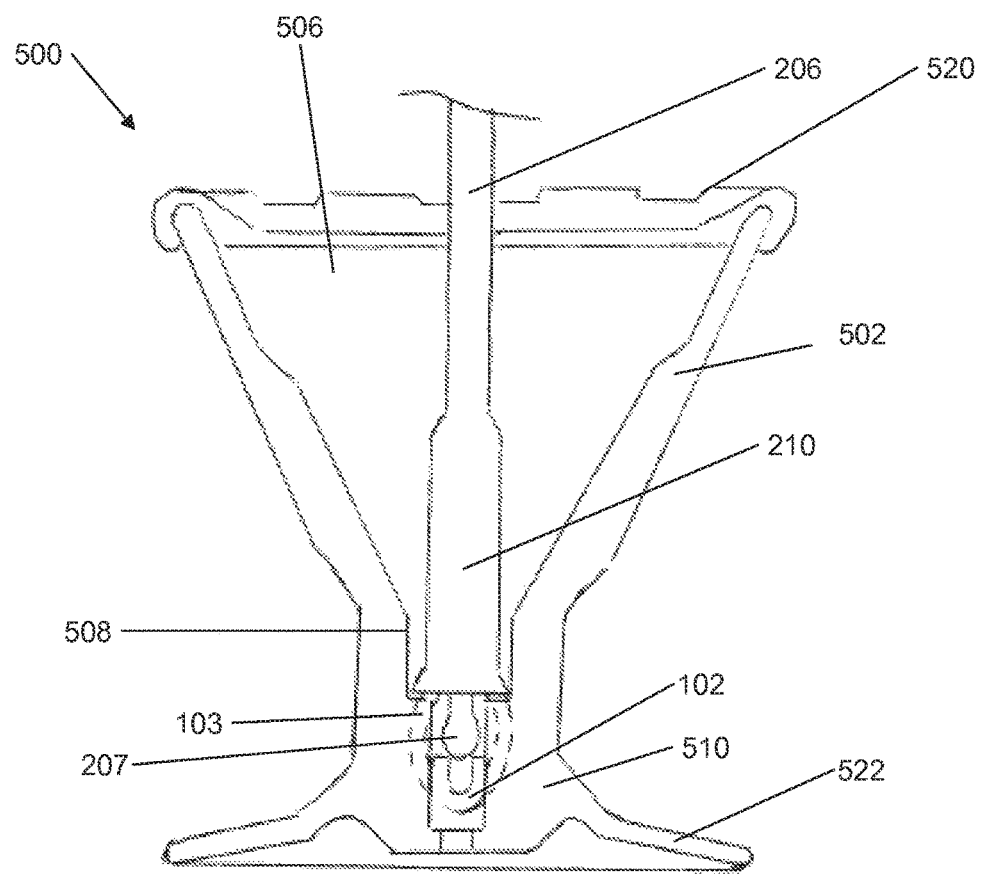

FIGS. 6A-6C depict a method by which the crimping device (500) may be used to crimp the implant (100) described above with respect to FIGS. 1 and 2A-2F from an expanded configuration to a low-profile configuration. It should be appreciated, however, that the crimping device (500) may be used to crimp any suitable implant. As shown in FIG. 6A, the implant (100) may first be placed in the first segment (506) of the crimping chamber (504). To place the implant (100) in the first segment (506), the implant (100) may be advanced through the proximal opening (512) of the crimping chamber (504). In some variations, the implant (100) may be temporarily moved toward a low-profile configuration (e.g., by temporarily flexing the legs (103) of the implant toward the longitudinal axis of the implant (100)) to allow the implant to enter the crimping chamber (504) through the proximal opening (512). In variations in which the crimping device (500) comprise a removable cap, the cap may be removed from the housing (502) to temporarily increase the size of the proximal opening (512). In some of these variations, the implant (100) may be inserted into the first segment (506) in an expanded (e.g., uncrimped) configuration, and the cap may then be replaced onto the proximal end of the housing (502). Generally, the lip (520) may hold the implant (100) in the crimping chamber (504) until the implant (100) is crimped to a low-profile configuration.

When the implant (100) is placed in the first segment (506) of the crimping chamber (504), the hub (102) of the implant (100) may be located distally relative to the legs (103) (i.e., toward the third segment (510)). One or more portions of the legs (103) (e.g., the proximal ends of the legs) may rest on the inner surface of the housing (502) within the first segment (506) when the implant (100) is positioned in the first segment (506), such as shown in FIG. 6A. In some variations, a portion of each leg (103) may be positioned at least partially in a channel (518) of the plurality of channels (518). In other variations (e.g., in variations where some or all of the first segment (506) does not include ribs (516) and channels (518)), the implant (100) may be positioned in the first segment (506) such that the legs (103) may rest against a portion of the first segment (506) that does not include ribs (516) and channels (518). For example, in some variations, the proximal ends of the legs (103) may rest against a wall of the housing (502) proximally of the plurality of ribs (516) and plurality of channels (518).

With the implant (100) positioned in the first segment (506), the delivery device (200) described above with respect to FIGS. 1, 3A, and 3B may be used to advance a portion of the implant (100) into the second segment (502). It should be appreciated that the crimping device (500) may be used in conjunction with any suitable delivery device, or may be operated independently of a delivery device. As shown in FIGS. 6A and 6B, a portion of the delivery device (200) may engage a portion of the implant (100) to advance the implant (100). For example, a distal tip of the inner shaft (204) (e.g., the ball tip (207)) may be placed into contact with a hub (102) (e.g., the proximal end of the hub (102)). The inner shaft (204) may be delivery device (200) may be advanced toward the second segment (508) to push the implant (100) toward the second segment (508) of the crimping chamber (504). As the hub (102) is advanced into the second segment (508), the legs (103) of the implant may be rotated toward the longitudinal axis of the implant (100) to move the implant toward the low-profile configuration. Specifically, as the portions of the legs (103) in contact with the outer diameter (only the inner diameters of the first, second, and third segments are illustrated in FIGS. 6A-6C) of the first segment (506) are moved toward the second segment (508), the tapering outer diameter of the first segment (506) may apply a radial force to push against the legs (103) to rotate the legs (103) toward the longitudinal axis of the implant (100). In variations where the first segment (506) includes a plurality of ribs (516) defining a plurality of channels (518), a portion of each of the legs (103) may be positioned in one of the channels (518). This may limit rotation of the implant (100) around the longitudinal axis of the implant (100), and may help to keep the implant (100) centered or otherwise aligned with the crimping device (500) during advancement of the implant (100). For example, positioning a portion of the legs (103) within the channels (518) may reduce the likelihood that the implant (100) will shift relative to the crimping device (500) during advancement and crimping of the implant (100). As mentioned above, in some of these variations, each leg (103) of the implant (100) may be positioned in a different channel (518), while in other variations, multiple legs (103) may be positioned in individual channels (518).

As portions of the legs (103) enter the second segment (508), the outer diameter of that portion of the implant (100) may be limited by the outer diameter of the second segment (508). In variations where the second segment (508) includes a plurality of ribs (516) defining a plurality of channels (518), a portion of each of the legs (103) may be positioned in one of the channels (518) (e.g., each leg (103) of the implant (100) may be positioned in a different channel (518) or multiple legs (103) may be positioned in individual channels (518)), which may help guide and align the implant (100).

Further advancement of the inner shaft (204) toward the third segment (510) may advance the hub (102) of the implant into the third segment (510), such as shown in FIG. 6B. In some variations, the third segment (510) may be sized such that at least a portion of some or all of the legs (103) remain in the second segment (508) when the hub (102) is advanced into the third segment (510). Additionally or alternatively, in variations where the third segment (510) has a smaller outer diameter than the outer diameter of the second segment (508), advancement of a portion of the legs (103) into the third segment (510) may further crimp the implant (100). In variations where the third segment (508) includes a plurality of ribs (516) defining a plurality of channels (518), a portion of each of the legs (103) may be positioned in one of the channels (518) (e.g., each leg (103) of the implant (100) may be positioned in a different channel (518) or multiple legs (103) may be positioned in individual channels (518)), which may help guide and align the implant (100). In variations where the plurality of ribs (516) and channels (518) extend from the first segment (506) to the third segment (510), each leg (103) may be advanced along the same channel (518) during advancement along the first, second, and third segments. In some variations, when the delivery device (200) and implant (100) are fully advanced into the crimping chamber (504), as shown in FIG. 6B, the distal end of the hub (102) of the implant (100) may pressed against the distal end (514) of the crimping chamber (504).

In variations where the delivery device (200) comprises and outer sheath (206), the inner shaft (204) may advance the hub (102) into the third segment (as discussed immediately above) with the outer sheath (206) retracted relative to the inner shaft (204). As the delivery device (200) and implant (100) are pushed toward the third segment (510), the legs (103) of the implant (100) may rotate relative to the hub (102) toward a low-profile (i.e., crimped) configuration, which in some instances may position a portion of each of the legs (103) into contact with or substantially parallel to the inner shaft (204) of the delivery device (200) (e.g., in some instances the legs may contact an engagement sleeve of the inner shaft). With the implant (100) positioned in a low-profile configuration, the outer sheath (206) may be advanced relative to the inner shaft (204) to cover at least a portion of the legs (103) with a portion of the outer sheath (206) (e.g., the distal cup (210) of the outer sheath (206)). This may act to hold the legs (103) of the implant (100) between the distal cup (210) and the inner shaft (204) of the delivery device (200), and thus may couple the implant (100) thereto, such as shown in FIG. 6C. In variations where the inner diameter of the third segment (510) is less than an outer diameter of the distal end of the outer sheath (e.g., the distal end of the distal cup (210)), the outer cup (210) may be prevented from entering the third segment (510). In some of these variations, the outer sheath (206) may be advanced until a distal end of the outer sheath (206) (e.g., the distal end of the outer cup (210)) contacts the ribs (516) of the third segment (510), such as shown in FIG. 6C.

With the delivery device (200) coupled to the implant (100), the delivery device (200) and implant (100) may be withdrawn relative to the crimping device (500). The delivery device (200) may then be used to deliver the implant (100) to a target location within a patient's body. To deliver the implant (100), the outer sheath (206) may be withdrawn (e.g., by retracting the outer sheath (206) relative to the inner shaft (204)) to expose the legs (103) of the implant. The implant (100) may then be expanded (either by self-expansion or via a device such as a balloon) in the patient to press against, dilate, or otherwise hold tissue in the patient.

The implants described here may be delivered to any suitable portion of the anatomy in any suitable manner. In some variations, the implant may be delivered to a sinus cavity or sinus ostium. In other variations, the implant may be delivered to a nasal cavity. In some variations, the implant may deliver, elute, or otherwise release one or more drugs therefrom when implanted.

The implants may be delivered and deployed in any suitable manner. In some variations, the implants are deployed in an open surgical fashion. In other variations, the implants are deployed in a less invasive fashion (for example, laproscopically, endoscopically, or intravascularly through the use of catheters). In instances where the implants are delivered in a generally minimally invasive fashion, the implants may be delivered in their low-profile configurations. The implants may be preloaded in or on a delivery device, but need not be. For example, in instances where the implant has a limited ability to fully expand after remaining in its compressed state for extended periods of time (i.e., relaxation of the implant may occur over time, resulting in a loss of shape memory, for example), it may be more desirable to crimp and load the implant into or onto a delivery device just prior to delivery and deployment.

Generally, at least a portion of a delivery device is introduced into the body. In some variations, the delivery device may be introduced into a natural opening in the body, such as an ear canal or a nostril. In other variations, the delivery device may be introduced into an opening in formed in the body via one or more procedures (e.g., a surgically-formed opening). In some of these variations, the artificially-created opening may be pre-formed using one or more tools that are separate from the delivery device. In some variations, one or more portions of the delivery device may be used to create the opening. In still other variations, one or more portions of the expandable device may be used to create the opening.

Once the delivery device is introduced into the body, at least a portion of the delivery device may then be advanced to a target location. In some variations, this advancement occurs under direct visualization. The direct visualization may be achieved by a device external to the delivery device, such as an endoscope, or may be achieved by one or more visualization devices attached to the delivery device or disposed within one or more portions (i.e., a lumen of a cannula) of the delivery device. In other variations, the advancement occurs under indirect visualization, such as fluoroscopy, ultrasound, or computer image guidance.

Once the delivery device is introduced into the body, at least a portion of the delivery device may then be advanced to a target location. In some variations, this advancement occurs under direct visualization. The direct visualization may be achieved by a device external to the delivery device, such as an endoscope, or may be achieved by one or more visualization devices attached to the delivery device or disposed within one or more portions (i.e., a lumen of a cannula) of the delivery device. In other variations, the advancement occurs under indirect visualization, such as fluoroscopy, ultrasound, or computer image guidance.

Once the delivery device has reached the target location, the expandable implant may be released from the delivery device. In variations where the implant is self-expandable, the implant may self-expand into an expanded configuration. In variations where the implant is expandable in response to one or more forces or stimuli, one or more appropriate forces or stimuli may be applied to the implant to expand the implant into an expanded configuration. In some instances, expansion of the implant may act to anchor the implant against or into tissue. The implant may be left in place for any suitable amount of time (e.g., one week, two weeks, one month, two months, or more). In variations where the implant is biodegradable, the implant may be removed prior to complete degradation of the implant, or may be left in place until the implant is absorbed or otherwise cleared by the body. When the implant is removed, it may be removed using a grasping device, pull-string structure, or the like.

When used to treat nasal polyposis or other polypoid adema one or more of the implant described here may be delivered into either a nasal passage or one or more sinus cavities. Once expanded, each leg of the implant may either sit against one or more nasal polyps, puncture one or more nasal polyps, push between two or more nasal polyps to contact the base of one or more nasal polyps, or do a combination thereof. When the implant is configured to deliver one or more drugs, it may be especially beneficial to deliver one or more drugs to the base of one or more of the nasal polyps. When one or more legs presses against one or more nasal polyps, the one or more legs may dilate or otherwise move the nasal polyps. This may, in turn, open one or more blocked nasal passageways or sinus ostia. It should be appreciated that the implants described here may be delivered using any of the methods described in U.S. patent application Ser. No. 12/779,240, which was previously incorporated by reference.

Although the foregoing invention has, for the purposes of clarity and understanding been described in some detail by way of illustration and example, it will be apparent that certain changes and modifications may be practiced, and are intended to fall within the scope of the appended claims.

We claim:

1. An expandable implant for placement in a sinus or a nasal cavity comprising:
   a hub, wherein the hub is formed from a biodegradable copolymer at a first composition ratio and comprises a plurality of apertures extending through the hub, each of said plurality of apertures comprising a first aperture segment and a second aperture segment separated by a hollow interior of the hub; and
   a plurality of filaments, wherein each filament of the plurality of filaments is formed from the biodegradable copolymer at a second composition ratio different from the first composition ratio, and wherein each filament of the plurality of filaments is positioned in a corresponding aperture of the plurality of apertures such that a portion of the filament extends through each of the first aperture segment, the second aperture segment, and the hollow interior of the hub to define a first leg on a first side of the hub and a second leg on a second side of the hub, and further wherein the expandable implant is sized and shaped for placement within the sinus or the nasal cavity.

2. The implant of claim 1 wherein each filament comprises a first straight segment, a second straight segment, and a curved segment positioned between the first straight segment and the second straight segment.

3. The implant of claim 2 wherein the curved segment of each filament is positioned in the corresponding aperture to position the first straight segment on the first side of the hub and the second straight segment on the second side of the hub.

4. The implant of claim 1 wherein each filament is an extruded polymer filament.

5. The implant of claim 4 wherein the hub is an injection molded hub.

6. The implant of claim 1 wherein the plurality of filaments are formed from one or more biodegradable materials.

7. The implant of claim 1 further comprising a drug-releasing coating.

8. The implant of claim 1 wherein the plurality of filaments form a plurality of legs having a first length and a second length, the first length being different from the second length.

9. The implant of claim 1 wherein the first length is about 20 mm and the second length is about 25 mm.

10. The implant of claim 1 wherein at least one of the plurality of filaments has a rectangular cross-sectional shape.

11. The implant of claim 1 wherein at least one of the plurality of filaments has an oval cross-sectional shape.

12. The implant of claim 1 wherein at least one of the plurality of filaments has a circular cross-sectional shape.

13. The implant of claim 1 wherein the drug-releasing coating comprises mometasone furoate.

\* \* \* \* \*